(12) United States Patent
Gamache et al.

(10) Patent No.: US 11,529,241 B2
(45) Date of Patent: Dec. 20, 2022

(54) FUSION CAGE WITH IN-LINE SINGLE PIECE FIXATION

(75) Inventors: Thomas Gamache, Raynham, MA (US); Joseph Childs, Raynham, MA (US); Matthew Parsons, Raynham, MA (US); Kevin Flaherty, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 13/237,174

(22) Filed: Sep. 20, 2011

(65) Prior Publication Data

US 2012/0078371 A1  Mar. 29, 2012

Related U.S. Application Data

(60) Provisional application No. 61/385,959, filed on Sep. 23, 2010, provisional application No. 61/466,309, (Continued)

(51) Int. Cl.
*A61F 2/44* (2006.01)
*A61F 2/46* (2006.01)
(Continued)

(52) U.S. Cl.
CPC ........ *A61F 2/4465* (2013.01); *A61B 17/0642* (2013.01); *A61B 17/0682* (2013.01);
(Continued)

(58) Field of Classification Search
CPC ........ A61F 2/441; A61F 2/442; A61F 2/4425; A61F 2/4455; A61F 2/446; A61F 2/4465; A61F 2/447; A61F 2002/443; A61F 2002/444; A61F 2002/448; A61F 2002/4611; A61F 2002/30484; A61F 2002/30604; A61F 2/44–2002/4475
(Continued)

(56) References Cited

U.S. PATENT DOCUMENTS

| 1,636,636 A | 12/1926 | Humble |
| 1,677,337 A | 7/1928 | Grove |

(Continued)

FOREIGN PATENT DOCUMENTS

| CN | 201244104 | 5/2009 |
| CN | 101951847 | 1/2011 |

(Continued)

OTHER PUBLICATIONS

Allcock, "Polyphosphazenes", The Encyclopedia of Polymer Science, vol. 13, pp. 31-41, Wiley Intersciences, John Wiley & Sons, (1988).

(Continued)

*Primary Examiner* — Si Ming Ku
*Assistant Examiner* — Tracy L Kamikawa

(57) ABSTRACT

Methods for securing a intervertebral cage to one or more levels of the spine with fixation. The fixation, which is typically a staple, is intended to be driven perpendicular to the proximal face of the cage and in-line with the inserter. After the cage is placed and positioned according to surgeon preference, a single piece fixation clip is then deployed and fixed in a manner that produces a zero-profile device.

2 Claims, 11 Drawing Sheets

Related U.S. Application Data filed on Mar. 22, 2011, provisional application No. 61/466,321, filed on Mar. 22, 2011.

(51) Int. Cl.

| | | |
|---|---|---|
| *A61B 17/064* | (2006.01) | |
| *A61B 17/068* | (2006.01) | |
| *A61F 2/30* | (2006.01) | |
| *A61F 2/28* | (2006.01) | |

(52) U.S. Cl.
CPC ..... *A61F 2/4611* (2013.01); *A61B 2017/0641* (2013.01); *A61F 2/4603* (2013.01); *A61F 2002/2835* (2013.01); *A61F 2002/30092* (2013.01); *A61F 2002/30161* (2013.01); *A61F 2002/30196* (2013.01); *A61F 2002/30484* (2013.01); *A61F 2002/30507* (2013.01); *A61F 2002/30518* (2013.01); *A61F 2002/30576* (2013.01); *A61F 2002/30579* (2013.01); *A61F 2002/30593* (2013.01); *A61F 2002/30604* (2013.01); *A61F 2002/30607* (2013.01); *A61F 2002/30616* (2013.01); *A61F 2002/30774* (2013.01); *A61F 2002/30787* (2013.01); *A61F 2002/30841* (2013.01); *A61F 2002/30843* (2013.01); *A61F 2002/30904* (2013.01); *A61F 2002/4625* (2013.01); *A61F 2310/00017* (2013.01); *A61F 2310/00023* (2013.01); *A61F 2310/00029* (2013.01); *A61F 2310/00161* (2013.01)

(58) Field of Classification Search
USPC ......... 606/75, 280, 281–284, 286, 297, 329; 623/17.11–17.16
See application file for complete search history.

(56) References Cited

U.S. PATENT DOCUMENTS

| | | |
|---|---|---|
| 2,304,703 A | 12/1942 | O'Leary |
| 4,105,034 A | 8/1978 | Shalaby |
| 4,130,639 A | 12/1978 | Shalaby |
| 4,140,678 A | 2/1979 | Shalaby |
| 4,141,087 A | 2/1979 | Shalaby |
| 4,205,399 A | 6/1980 | Shalaby |
| 4,208,511 A | 6/1980 | Shalaby |
| 4,743,256 A | 5/1988 | Brantigan |
| 4,904,261 A | 2/1990 | Dove |
| 4,946,378 A | 8/1990 | Hirayama |
| 4,955,908 A | 9/1990 | Frey |
| 5,041,113 A | 8/1991 | Biedermann |
| 5,123,926 A | 6/1992 | Pisharodi |
| 5,147,361 A | 9/1992 | Ojima et al. |
| 5,209,751 A | 5/1993 | Farris |
| 5,306,308 A | 4/1994 | Gross |
| 5,352,231 A | 10/1994 | Brumfield |
| 5,391,170 A | 2/1995 | McGuire |
| 5,395,372 A | 3/1995 | Holt |
| 5,397,364 A | 3/1995 | Kozak |
| 5,443,514 A | 8/1995 | Steffee |
| 5,443,515 A | 8/1995 | Cohen |
| 5,464,407 A | 11/1995 | McGuire |
| 5,464,929 A | 11/1995 | Bezwada |
| 5,499,986 A | 3/1996 | Dimarco |
| 5,529,580 A | 6/1996 | Kusunoki |
| 5,534,031 A | 7/1996 | Matsuzaki |
| 5,578,034 A | 11/1996 | Estes |
| 5,591,166 A | 1/1997 | Bernhardt et al. |
| 5,595,751 A | 1/1997 | Bezwada |
| 5,597,579 A | 1/1997 | Bezwada |
| 5,601,553 A | 2/1997 | Trebing et al. |
| 5,607,687 A | 3/1997 | Bezwada |
| 5,609,636 A | 3/1997 | Kohrs et al. |
| 5,618,552 A | 4/1997 | Bezwada |
| 5,620,458 A | 4/1997 | Green et al. |
| 5,620,698 A | 4/1997 | Bezwada |
| 5,645,598 A | 7/1997 | Brosnahan, III |
| 5,645,850 A | 7/1997 | Bezwada |
| 5,648,088 A | 7/1997 | Bezwada |
| 5,662,655 A | 9/1997 | Laboureau |
| 5,676,666 A | 10/1997 | Oxland |
| 5,698,213 A | 12/1997 | Jamiolkowski |
| 5,700,583 A | 12/1997 | Jamiolkowski |
| 5,713,899 A * | 2/1998 | Marnay ................. A61F 2/4455 623/17.11 |
| 5,716,415 A | 2/1998 | Steffee |
| 5,755,796 A | 5/1998 | Ibo et al. |
| 5,776,196 A | 7/1998 | Matsuzaki |
| 5,779,707 A | 7/1998 | Bertholet |
| 5,785,713 A | 7/1998 | Jobe |
| 5,788,698 A | 8/1998 | Savornin |
| 5,797,912 A | 8/1998 | Runciman |
| 5,797,918 A | 8/1998 | McGuire |
| 5,800,435 A | 9/1998 | Errico et al. |
| 5,800,440 A | 9/1998 | Stead |
| 5,859,150 A | 1/1999 | Jamiolkowski |
| 5,888,223 A | 3/1999 | Bray, Jr. |
| 5,893,889 A | 4/1999 | Harrington |
| 5,904,689 A | 5/1999 | Jonjic |
| 5,913,860 A | 6/1999 | Scholl |
| 6,039,761 A | 3/2000 | Li et al. |
| 6,049,026 A | 4/2000 | Muschler |
| 6,056,749 A | 5/2000 | Kuslich |
| 6,066,175 A | 5/2000 | Henderson |
| 6,086,593 A | 7/2000 | Bonutti |
| 6,093,205 A | 7/2000 | McLeod |
| 6,099,531 A * | 8/2000 | Bonutti ................. A61B 17/562 606/87 |
| 6,106,557 A | 8/2000 | Robioneck |
| 6,117,174 A | 9/2000 | Nolan |
| 6,120,503 A | 9/2000 | Michelson |
| 6,126,689 A | 10/2000 | Brett |
| 6,127,597 A | 10/2000 | Beyar et al. |
| 6,139,550 A | 10/2000 | Michelson |
| 6,156,037 A | 12/2000 | LeHuec |
| 6,159,211 A | 12/2000 | Boriani |
| 6,159,244 A | 12/2000 | Suddaby |
| 6,174,311 B1 | 1/2001 | Branch et al. |
| 6,179,875 B1 | 1/2001 | Von Strempel |
| 6,190,414 B1 | 2/2001 | Young et al. |
| 6,193,757 B1 | 2/2001 | Foley et al. |
| 6,200,306 B1 | 3/2001 | Klostermeyer |
| 6,206,922 B1 | 3/2001 | Zdeblick |
| 6,224,602 B1 | 5/2001 | Hayes |
| 6,224,631 B1 | 5/2001 | Kohrs |
| 6,231,610 B1 | 5/2001 | Geisler |
| 6,235,059 B1 | 5/2001 | Benezech |
| 6,306,170 B2 | 10/2001 | Ray |
| 6,330,845 B1 | 12/2001 | Meulink |
| 6,336,928 B1 | 1/2002 | Guerin |
| 6,342,055 B1 | 1/2002 | Eisermann |
| 6,342,074 B1 | 1/2002 | Simpson |
| 6,364,880 B1 | 4/2002 | Michelson |
| 6,368,351 B1 | 4/2002 | Glenn et al. |
| 6,375,462 B2 | 4/2002 | Holweg et al. |
| 6,387,130 B1 | 5/2002 | Stone |
| 6,395,031 B1 | 5/2002 | Foley et al. |
| 6,406,478 B1 | 6/2002 | Kuo |
| 6,409,766 B1 | 6/2002 | Brett |
| 6,413,278 B1 | 7/2002 | Marchosky |
| 6,423,063 B1 * | 7/2002 | Bonutti ................. A61B 17/562 606/60 |
| 6,428,575 B2 | 8/2002 | Koo |
| 6,432,106 B1 | 8/2002 | Fraser |
| 6,447,544 B1 | 9/2002 | Michelson |
| 6,447,546 B1 * | 9/2002 | Bramlet ................. A61F 2/446 623/17.11 |
| 6,454,769 B2 | 9/2002 | Wagner |
| 6,461,359 B1 | 10/2002 | Tribus |
| 6,471,724 B2 | 10/2002 | Zdeblick |
| 6,488,710 B2 | 12/2002 | Besselink |
| 6,508,818 B2 | 1/2003 | Steiner et al. |

(56) References Cited

U.S. PATENT DOCUMENTS

| | | | |
|---|---|---|---|
| 6,558,387 | B2 | 5/2003 | Errico |
| 6,558,423 | B1 | 5/2003 | Michelson |
| 6,562,073 | B2 | 5/2003 | Foley |
| 6,565,570 | B2 | 5/2003 | Sterett |
| 6,572,619 | B2 | 6/2003 | Santilli |
| 6,579,290 | B1 | 6/2003 | Hardcastle |
| 6,579,321 | B1 | 6/2003 | Gordon et al. |
| 6,592,624 | B1 | 7/2003 | Fraser et al. |
| 6,602,257 | B1 | 8/2003 | Thramann |
| 6,629,998 | B1 | 10/2003 | Lin |
| 6,679,915 | B1 | 1/2004 | Cauthen |
| 6,682,563 | B2 | 1/2004 | Scharf |
| 6,695,846 | B2 | 2/2004 | Richelsoph |
| 6,730,125 | B1 | 5/2004 | Lin |
| 6,730,127 | B2 | 5/2004 | Michelson |
| 6,733,531 | B1 | 5/2004 | Trieu |
| 6,736,850 | B2 | 5/2004 | Davis |
| 6,743,257 | B2 | 6/2004 | Castro |
| 6,745,255 | B2 | 6/2004 | Yen et al. |
| 6,761,738 | B1 | 7/2004 | Boyd |
| 6,770,096 | B2 * | 8/2004 | Bolger ............ A61B 17/0206 623/17.16 |
| 6,773,437 | B2 | 8/2004 | Ogilvie |
| 6,776,781 | B1 | 8/2004 | Uwaydah |
| 6,805,714 | B2 | 10/2004 | Sutcliffe |
| 6,808,537 | B2 | 10/2004 | Michelson |
| 6,824,564 | B2 | 11/2004 | Crozet |
| 6,824,565 | B2 | 11/2004 | Muhanna et al. |
| 6,833,006 | B2 | 12/2004 | Foley et al. |
| 6,835,208 | B2 | 12/2004 | Marchosky |
| 6,837,905 | B1 | 1/2005 | Lieberman |
| 6,849,093 | B2 * | 2/2005 | Michelson ............ A61F 2/446 623/17.11 |
| 6,890,335 | B2 | 5/2005 | Grabowski |
| 6,890,355 | B2 | 5/2005 | Michelson |
| 6,945,973 | B2 | 9/2005 | Bray |
| 6,972,019 | B2 | 12/2005 | Michelson |
| 6,974,479 | B2 | 12/2005 | Trieu |
| 6,974,480 | B2 | 12/2005 | Messerli et al. |
| 6,984,234 | B2 | 1/2006 | Bray |
| 7,001,385 | B2 | 2/2006 | Bonutti |
| 7,033,394 | B2 | 4/2006 | Michelson |
| 7,041,135 | B2 | 5/2006 | Michelson |
| 7,044,971 | B2 | 5/2006 | Suddaby |
| 7,056,341 | B2 | 6/2006 | Crozet |
| 7,063,491 | B2 | 6/2006 | French |
| 7,070,598 | B2 | 7/2006 | Lim et al. |
| 7,077,864 | B2 | 7/2006 | Byrd, III |
| 7,087,055 | B2 | 8/2006 | Lim et al. |
| 7,112,222 | B2 | 9/2006 | Fraser |
| 7,112,223 | B2 | 9/2006 | Davis |
| 7,135,024 | B2 | 11/2006 | Cook |
| 7,135,043 | B2 | 11/2006 | Nakahara |
| 7,163,561 | B2 | 1/2007 | Michelson |
| 7,172,627 | B2 | 2/2007 | Fiere |
| 7,226,482 | B2 | 6/2007 | Messerli |
| 7,232,463 | B2 | 6/2007 | Falahee |
| 7,232,464 | B2 | 6/2007 | Mathieu |
| 7,238,203 | B2 | 7/2007 | Bagga |
| 7,238,206 | B2 | 7/2007 | Lange |
| 7,255,698 | B2 | 8/2007 | Michelson |
| 7,276,081 | B1 | 10/2007 | Coates |
| 7,288,094 | B2 | 10/2007 | Lindemann |
| 7,288,095 | B2 | 10/2007 | Baynam et al. |
| 7,288,114 | B2 | 10/2007 | Lange |
| 7,306,605 | B2 | 12/2007 | Ross |
| 7,309,358 | B2 | 12/2007 | Berry |
| 7,311,734 | B2 | 12/2007 | Van Hoeck |
| 7,316,714 | B2 | 1/2008 | Gordon |
| 7,318,839 | B2 | 1/2008 | Malberg et al. |
| 7,323,011 | B2 | 1/2008 | Shepard |
| 7,326,248 | B2 | 2/2008 | Michelson |
| 7,332,209 | B2 | 2/2008 | Yokouchi |
| 7,338,525 | B2 | 3/2008 | Ferree |
| 7,341,587 | B2 | 3/2008 | Molz, IV |
| 7,341,590 | B2 | 3/2008 | Ferree |
| 7,354,452 | B2 | 4/2008 | Foley |
| 7,361,193 | B2 | 4/2008 | Frey |
| 7,435,262 | B2 | 10/2008 | Michelson |
| 7,438,715 | B2 | 10/2008 | Doubler |
| 7,442,209 | B2 | 10/2008 | Michelson |
| 7,452,370 | B2 | 11/2008 | Anderson |
| 7,491,237 | B2 | 2/2009 | Randall |
| 7,513,900 | B2 | 4/2009 | Carrison et al. |
| 7,527,641 | B2 | 5/2009 | Suh |
| 7,594,931 | B2 | 9/2009 | Louis |
| 7,594,932 | B2 | 9/2009 | Aferzon |
| 7,601,171 | B2 | 10/2009 | Ainsworth et al. |
| 7,601,173 | B2 | 10/2009 | Messerli |
| 7,608,062 | B2 | 10/2009 | Sweeney |
| 7,618,456 | B2 | 11/2009 | Mathieu |
| 7,628,816 | B2 | 12/2009 | Magerl |
| 7,641,665 | B2 | 1/2010 | Zubok |
| 7,655,042 | B2 | 2/2010 | Foley et al. |
| 7,658,766 | B2 | 2/2010 | Melkent |
| 7,662,182 | B2 | 2/2010 | Zubok |
| 7,674,279 | B2 | 3/2010 | Johnson |
| 7,704,255 | B2 | 4/2010 | Michelson |
| 7,726,002 | B2 | 6/2010 | Shimp |
| 7,794,502 | B2 | 9/2010 | Michelson |
| 7,815,643 | B2 | 10/2010 | Johnson et al. |
| 7,815,681 | B2 | 10/2010 | Ferguson |
| 7,846,206 | B2 | 12/2010 | Leonard et al. |
| 7,846,210 | B2 | 12/2010 | Perez-Cruet et al. |
| 7,862,616 | B2 | 1/2011 | Lechmann et al. |
| 7,871,441 | B2 | 1/2011 | Eckman |
| 7,875,062 | B2 | 1/2011 | Lindemann |
| 7,875,076 | B2 | 1/2011 | Mathieu |
| 7,883,531 | B2 | 2/2011 | Coninck |
| 7,887,591 | B2 | 2/2011 | Aebi et al. |
| 7,887,595 | B1 | 2/2011 | Pimenta |
| 7,909,877 | B2 | 3/2011 | Krueger et al. |
| 7,942,903 | B2 | 5/2011 | Moskowitz |
| 7,993,403 | B2 | 8/2011 | Foley et al. |
| 8,002,808 | B2 | 8/2011 | Morrison et al. |
| 8,007,523 | B2 | 8/2011 | Wagner |
| 8,070,815 | B2 * | 12/2011 | Yu ............ A61F 2/4425 623/17.11 |
| 8,187,329 | B2 | 5/2012 | Theofilos |
| 8,206,423 | B2 | 6/2012 | Siegal |
| 8,216,312 | B2 | 7/2012 | Gray |
| 8,236,029 | B2 | 8/2012 | Siegal |
| 8,241,328 | B2 | 8/2012 | Siegal |
| 8,246,622 | B2 | 8/2012 | Siegal et al. |
| 8,257,439 | B2 * | 9/2012 | Zeegers ............ A61B 17/0642 623/17.14 |
| 8,282,641 | B2 | 10/2012 | Lopez et al. |
| 8,323,342 | B2 | 12/2012 | Schwab |
| 8,328,812 | B2 | 12/2012 | Siegal et al. |
| 8,336,559 | B2 | 12/2012 | Kallabat et al. |
| 8,337,559 | B2 | 12/2012 | Hansell et al. |
| 8,343,219 | B2 | 1/2013 | Allain |
| 8,349,015 | B2 | 1/2013 | Bae et al. |
| 8,357,200 | B2 | 1/2013 | Adi |
| 8,377,133 | B2 | 2/2013 | Yuan et al. |
| 8,454,694 | B2 | 6/2013 | Armstrong et al. |
| 8,460,385 | B1 | 6/2013 | Wensel |
| 8,460,387 | B2 | 6/2013 | Theofilos |
| 8,460,388 | B2 | 6/2013 | Kirwan |
| 8,465,524 | B2 | 6/2013 | Siegal |
| 8,470,044 | B2 | 6/2013 | Bertholet et al. |
| 8,480,747 | B2 | 7/2013 | Melkent et al. |
| 8,486,109 | B2 | 7/2013 | Siegal |
| 8,491,653 | B2 | 7/2013 | Zucherman et al. |
| 8,491,658 | B1 | 7/2013 | Etminan |
| 8,496,691 | B2 | 7/2013 | Blain |
| 8,496,708 | B2 | 7/2013 | Blain |
| 8,500,783 | B2 | 8/2013 | Baynham |
| 8,540,769 | B2 | 9/2013 | Janowski |
| 8,551,175 | B1 | 10/2013 | Wensel |
| 8,562,651 | B2 | 10/2013 | Metcalf et al. |
| 8,597,330 | B2 | 12/2013 | Siegal |
| 8,613,772 | B2 | 12/2013 | Bray et al. |
| 8,617,245 | B2 | 12/2013 | Brett |

(56) References Cited

U.S. PATENT DOCUMENTS

| | | | |
|---|---|---|---|
| 8,628,578 B2 | 1/2014 | Miller et al. | |
| 8,641,765 B2 | 2/2014 | Muhanna | |
| 8,672,977 B2 | 3/2014 | Siegal et al. | |
| 8,690,928 B1 | 4/2014 | Walkenhorst et al. | |
| 8,690,948 B2 | 4/2014 | Armstrong et al. | |
| 8,747,443 B2 | 6/2014 | Aferzon | |
| 8,758,439 B2 | 6/2014 | Linares | |
| 8,777,993 B2 | 7/2014 | Siegal et al. | |
| 8,821,555 B2 | 9/2014 | Bae | |
| 8,845,638 B2 | 9/2014 | Siegal et al. | |
| 8,900,235 B2 | 12/2014 | Siegal | |
| 8,906,098 B2 | 12/2014 | Siegal | |
| 8,932,358 B1 | 1/2015 | Nehls | |
| 8,932,359 B2 | 1/2015 | Brett | |
| 8,956,416 B2 | 2/2015 | McCarthy | |
| 9,005,293 B2 | 4/2015 | Moskowitz et al. | |
| 9,005,295 B2 | 4/2015 | Kueenzi et al. | |
| 9,017,408 B2 | 4/2015 | Siegal et al. | |
| 9,017,413 B2 | 4/2015 | Siegal et al. | |
| 9,039,768 B2 | 5/2015 | Voellmicke | |
| 9,044,334 B2 | 6/2015 | Siegal et al. | |
| 9,138,330 B2 | 9/2015 | Hansell et al. | |
| 9,192,419 B2 | 11/2015 | McDonough et al. | |
| 9,248,028 B2 | 2/2016 | Gamache | |
| 9,254,138 B2 | 2/2016 | Siegal et al. | |
| 9,265,546 B2 | 2/2016 | Blain | |
| 9,265,621 B2 | 2/2016 | Voellmicke | |
| 9,271,836 B2 | 2/2016 | Gamache | |
| 9,278,009 B2 | 3/2016 | Bray et al. | |
| 9,283,091 B2 | 3/2016 | Melkent | |
| 9,283,092 B2 | 3/2016 | Siegal et al. | |
| 9,289,311 B1 | 3/2016 | Whipple | |
| 9,292,419 B1 | 3/2016 | Kintali et al. | |
| 9,364,272 B2 | 6/2016 | Binder et al. | |
| 9,402,735 B2 | 8/2016 | McDonough et al. | |
| 9,402,738 B2 | 8/2016 | Niemie | |
| 9,408,712 B2 | 8/2016 | Siegal et al. | |
| 9,445,918 B1 | 9/2016 | Lin et al. | |
| 9,492,286 B2 | 11/2016 | Biedermann et al. | |
| 9,566,165 B2 | 2/2017 | Lee et al. | |
| 9,592,129 B2 | 3/2017 | Slivka et al. | |
| 9,662,225 B2 | 5/2017 | Pavento | |
| 9,668,877 B2 | 6/2017 | Pavento | |
| 9,848,992 B2 | 12/2017 | McDonough | |
| 9,867,718 B2 | 1/2018 | Schmura | |
| 9,872,781 B2 | 1/2018 | Pavento | |
| 9,918,851 B2 | 3/2018 | Willis et al. | |
| 9,987,142 B2 | 6/2018 | McConnell | |
| 10,327,915 B2 | 6/2019 | Pavento | |
| 2001/0016775 A1 | 8/2001 | Scarborough et al. | |
| 2001/0031968 A1 | 10/2001 | Dorchak et al. | |
| 2001/0032020 A1 | 10/2001 | Besselink | |
| 2002/0029044 A1 | 3/2002 | Monassevitch | |
| 2002/0029082 A1 | 3/2002 | Muhanna | |
| 2002/0082693 A1 | 6/2002 | Ahlgren | |
| 2002/0095155 A1 | 7/2002 | Michelson | |
| 2002/0099376 A1 | 7/2002 | Michelson | |
| 2002/0138146 A1 | 9/2002 | Jackson | |
| 2002/0143328 A1 | 10/2002 | Shulzas | |
| 2002/0151976 A1 | 10/2002 | Foley et al. | |
| 2002/0156475 A1 | 10/2002 | Lerch | |
| 2003/0004576 A1 | 1/2003 | Thalgott | |
| 2003/0014113 A1 | 1/2003 | Ralph | |
| 2003/0028197 A1 | 2/2003 | Hanson | |
| 2003/0045940 A1 | 3/2003 | Eberlein | |
| 2003/0050645 A1 | 3/2003 | Parker | |
| 2003/0083748 A1 | 5/2003 | Lee et al. | |
| 2003/0100949 A1 | 5/2003 | Michelson | |
| 2003/0125739 A1 | 7/2003 | Bagga | |
| 2003/0130739 A1 | 7/2003 | Gerbec et al. | |
| 2003/0153975 A1 | 8/2003 | Byrd | |
| 2003/0158555 A1 | 8/2003 | Sanders | |
| 2003/0187440 A1 | 10/2003 | Richelsoph et al. | |
| 2003/0187506 A1 | 10/2003 | Ross | |
| 2003/0195632 A1 | 10/2003 | Foley | |
| 2003/0208203 A1 | 11/2003 | Lim | |
| 2003/0225409 A1 | 12/2003 | Freid | |
| 2004/0024464 A1 | 2/2004 | Errico | |
| 2004/0034430 A1 | 2/2004 | Falahee | |
| 2004/0068318 A1 | 4/2004 | Coates et al. | |
| 2004/0073213 A1 | 4/2004 | Serhan | |
| 2004/0088055 A1 | 5/2004 | Hanson et al. | |
| 2004/0092929 A1 | 5/2004 | Zindrick | |
| 2004/0106996 A1 | 6/2004 | Liu et al. | |
| 2004/0111089 A1 | 6/2004 | Stevens et al. | |
| 2004/0117022 A1 | 6/2004 | Marnay et al. | |
| 2004/0127902 A1 | 7/2004 | Suzuki | |
| 2004/0127990 A1 | 7/2004 | Bartish | |
| 2004/0138662 A1 | 7/2004 | Landry et al. | |
| 2004/0153065 A1 | 8/2004 | Lim | |
| 2004/0153072 A1* | 8/2004 | Bonutti | A61B 17/562 606/247 |
| 2004/0162618 A1 | 8/2004 | Mujwid et al. | |
| 2004/0167625 A1 | 8/2004 | Beyar et al. | |
| 2004/0193269 A1 | 9/2004 | Fraser et al. | |
| 2004/0193271 A1 | 9/2004 | Fraser et al. | |
| 2004/0199253 A1 | 10/2004 | Link | |
| 2004/0199254 A1 | 10/2004 | Louis | |
| 2004/0210219 A1 | 10/2004 | Bray | |
| 2004/0230309 A1 | 11/2004 | DiMauro | |
| 2004/0249377 A1 | 12/2004 | Kaes | |
| 2004/0254644 A1 | 12/2004 | Taylor | |
| 2004/0260286 A1 | 12/2004 | Ferree | |
| 2005/0015147 A1 | 1/2005 | Schwardt et al. | |
| 2005/0021144 A1 | 1/2005 | Malberg et al. | |
| 2005/0033433 A1 | 2/2005 | Michelson | |
| 2005/0038513 A1 | 2/2005 | Michelson | |
| 2005/0043800 A1 | 2/2005 | Paul et al. | |
| 2005/0060034 A1 | 3/2005 | Berry | |
| 2005/0065608 A1 | 3/2005 | Michelson | |
| 2005/0071006 A1 | 3/2005 | Kirschman | |
| 2005/0071008 A1 | 3/2005 | Kirschman | |
| 2005/0085913 A1 | 4/2005 | Fraser | |
| 2005/0096657 A1 | 5/2005 | Autericque | |
| 2005/0101960 A1 | 5/2005 | Fiere | |
| 2005/0113920 A1 | 5/2005 | Foley et al. | |
| 2005/0143749 A1 | 6/2005 | Zalenski | |
| 2005/0143827 A1 | 6/2005 | Globerman | |
| 2005/0149192 A1 | 7/2005 | Zucherman | |
| 2005/0149193 A1 | 7/2005 | Zucherman | |
| 2005/0154391 A1 | 7/2005 | Doherty | |
| 2005/0159813 A1 | 7/2005 | Molz | |
| 2005/0159819 A1 | 7/2005 | McCormack et al. | |
| 2005/0165483 A1 | 7/2005 | Ray et al. | |
| 2005/0177240 A1 | 8/2005 | Blain | |
| 2005/0177245 A1 | 8/2005 | Leatherbury | |
| 2005/0182416 A1 | 8/2005 | Lim et al. | |
| 2005/0203515 A1 | 9/2005 | Doherty et al. | |
| 2005/0209696 A1 | 9/2005 | Lin et al. | |
| 2005/0216081 A1 | 9/2005 | Taylor | |
| 2005/0251260 A1 | 11/2005 | Gerber | |
| 2005/0261768 A1 | 11/2005 | Trieu | |
| 2005/0277938 A1 | 12/2005 | Parsons | |
| 2005/0278036 A1 | 12/2005 | Leonard | |
| 2006/0025860 A1 | 2/2006 | Li | |
| 2006/0030851 A1 | 2/2006 | Bray | |
| 2006/0036256 A1 | 2/2006 | Carl et al. | |
| 2006/0036261 A1 | 2/2006 | McDonnell | |
| 2006/0058801 A1 | 3/2006 | Schlienger et al. | |
| 2006/0079961 A1 | 4/2006 | Michelson | |
| 2006/0085071 A1 | 4/2006 | Lechmann | |
| 2006/0116研究 A1 | 6/2006 | Krueger | |
| 2006/0129424 A1 | 6/2006 | Chan | |
| 2006/0136063 A1* | 6/2006 | Zeegers | A61B 17/0642 623/17.14 |
| 2006/0142765 A9 | 6/2006 | Dixon | |
| 2006/0142858 A1 | 6/2006 | Colleran et al. | |
| 2006/0142863 A1 | 6/2006 | Fraser | |
| 2006/0152863 A1 | 6/2006 | Fraser | |
| 2006/0178745 A1 | 8/2006 | Bartish | |
| 2006/0190083 A1 | 8/2006 | Arnin | |
| 2006/0211952 A1 | 9/2006 | Kennedy | |
| 2006/0229609 A1 | 10/2006 | Wang | |
| 2006/0229724 A1 | 10/2006 | Lechmann et al. | |

(56) References Cited

U.S. PATENT DOCUMENTS

| | | |
|---|---|---|
| 2006/0229729 A1 | 10/2006 | Gordon et al. |
| 2006/0235403 A1 | 10/2006 | Blain |
| 2006/0235409 A1 | 10/2006 | Blain |
| 2006/0235411 A1 | 10/2006 | Blain |
| 2006/0235518 A1 | 10/2006 | Blain |
| 2006/0235535 A1 | 10/2006 | Ferree |
| 2006/0241597 A1 | 10/2006 | Mitchell et al. |
| 2006/0241761 A1 | 10/2006 | Gately |
| 2006/0247650 A1 | 11/2006 | Yerby et al. |
| 2006/0259147 A1 | 11/2006 | Krishna |
| 2006/0265068 A1 | 11/2006 | Schwab |
| 2006/0293753 A1 | 12/2006 | Thramann |
| 2007/0049941 A1 | 3/2007 | Thramann |
| 2007/0055252 A1 | 3/2007 | Thramann |
| 2007/0067035 A1 | 3/2007 | Falahee |
| 2007/0073398 A1 | 3/2007 | Fabian et al. |
| 2007/0213820 A1 | 3/2007 | Blain |
| 2007/0106384 A1 | 5/2007 | Bray |
| 2007/0106388 A1 | 5/2007 | Michelson |
| 2007/0129804 A1 | 6/2007 | Bentley |
| 2007/0149978 A1 | 6/2007 | Shezifi |
| 2007/0162138 A1 | 7/2007 | Heinz |
| 2007/0198016 A1 | 8/2007 | Zang |
| 2007/0213737 A1 | 9/2007 | Schemmerhorn et al. |
| 2007/0219635 A1 | 9/2007 | Mathieu |
| 2007/0233118 A1 | 10/2007 | Mclain |
| 2007/0233253 A1 | 10/2007 | Bray |
| 2007/0233254 A1 | 10/2007 | Grotz |
| 2007/0233261 A1 | 10/2007 | Lopez et al. |
| 2007/0233263 A1 | 10/2007 | Melkent |
| 2007/0239278 A1* | 10/2007 | Heinz ............... A61F 2/4425 623/17.15 |
| 2007/0250167 A1 | 10/2007 | Bray |
| 2007/0255416 A1 | 11/2007 | Melkent |
| 2007/0265631 A1 | 11/2007 | Fox |
| 2007/0270957 A1 | 11/2007 | Heinz |
| 2007/0270965 A1 | 11/2007 | Ferguson |
| 2007/0276490 A1 | 11/2007 | Mateyka |
| 2007/0282443 A1 | 12/2007 | Globerman et al. |
| 2007/0282449 A1 | 12/2007 | De Villiers et al. |
| 2007/0293948 A1 | 12/2007 | Bagga |
| 2007/0299521 A1 | 12/2007 | Glenn et al. |
| 2008/0015694 A1 | 1/2008 | Tribus |
| 2008/0015701 A1 | 1/2008 | Garcia |
| 2008/0021476 A1 | 1/2008 | Kirschman |
| 2008/0027550 A1 | 1/2008 | Link |
| 2008/0140085 A1 | 1/2008 | Gately |
| 2008/0033440 A1 | 2/2008 | Moskowitz |
| 2008/0033480 A1 | 2/2008 | Hardert |
| 2008/0051890 A1 | 2/2008 | Waugh |
| 2008/0051897 A1 | 2/2008 | Lopez et al. |
| 2008/0065219 A1 | 3/2008 | Dye |
| 2008/0077247 A1 | 3/2008 | Murillo |
| 2008/0082173 A1 | 4/2008 | Delurio |
| 2008/0097436 A1 | 4/2008 | Culbert |
| 2008/0103597 A1 | 5/2008 | Lechman et al. |
| 2008/0103598 A1 | 5/2008 | Bao |
| 2008/0109005 A1 | 5/2008 | Trudeau et al. |
| 2008/0119933 A1 | 5/2008 | Aebi |
| 2008/0125865 A1 | 5/2008 | Abdelgany |
| 2008/0132949 A1 | 6/2008 | Aferzon |
| 2008/0132958 A1 | 6/2008 | Pech |
| 2008/0133012 A1 | 6/2008 | McGuckin |
| 2008/0133014 A1 | 6/2008 | Gately et al. |
| 2008/0154379 A1 | 6/2008 | Steiner |
| 2008/0161922 A1 | 7/2008 | Rhoda |
| 2008/0161925 A1 | 7/2008 | Brittan |
| 2008/0167666 A1* | 7/2008 | Fiere ............... A61B 17/0642 606/151 |
| 2008/0172128 A1 | 7/2008 | Perez-Cruet |
| 2008/0177307 A1 | 7/2008 | Moskowitz |
| 2008/0183293 A1* | 7/2008 | Parry ............... A61F 2/447 623/17.11 |
| 2008/0183294 A1 | 7/2008 | Adi |
| 2008/0221690 A1 | 9/2008 | Chaput |
| 2008/0221694 A1 | 9/2008 | Warnick et al. |
| 2008/0234822 A1 | 9/2008 | Govil |
| 2008/0243136 A1 | 10/2008 | Prager |
| 2008/0249569 A1 | 10/2008 | Waugh |
| 2008/0249575 A1 | 10/2008 | Waugh |
| 2008/0249625 A1 | 10/2008 | Waugh |
| 2008/0255620 A1 | 10/2008 | Strauss |
| 2008/0269806 A1 | 10/2008 | Zhang |
| 2008/0281425 A1 | 11/2008 | Thalgott |
| 2008/0294262 A1 | 11/2008 | Levieux |
| 2008/0300601 A1 | 12/2008 | Fabian et al. |
| 2008/0300634 A1 | 12/2008 | Gray |
| 2008/0306596 A1 | 12/2008 | Jones |
| 2008/0306598 A1 | 12/2008 | Hansen |
| 2008/0312698 A1 | 12/2008 | Bergeron |
| 2008/0312742 A1 | 12/2008 | Abernathie |
| 2008/0312743 A1 | 12/2008 | Vila et al. |
| 2009/0012529 A1 | 1/2009 | Blain |
| 2009/0030421 A1 | 1/2009 | Hawkins |
| 2009/0030519 A1 | 1/2009 | Falahee |
| 2009/0030520 A1 | 1/2009 | Biedermann |
| 2009/0062921 A1 | 3/2009 | Michelson |
| 2009/0069895 A1 | 3/2009 | Gittings |
| 2009/0088849 A1 | 4/2009 | Armstrong |
| 2009/0099554 A1 | 4/2009 | Forster |
| 2009/0099610 A1 | 4/2009 | Johnson et al. |
| 2009/0099661 A1 | 4/2009 | Bhattacharya |
| 2009/0105771 A1 | 4/2009 | Lei |
| 2009/0105774 A1 | 4/2009 | Jones |
| 2009/0105830 A1 | 4/2009 | Jones |
| 2009/0105831 A1 | 4/2009 | Jones |
| 2009/0105832 A1* | 4/2009 | Allain ............... A61B 17/0642 623/17.16 |
| 2009/0125028 A1 | 5/2009 | Teisen et al. |
| 2009/0131988 A1 | 5/2009 | Bush, Jr. |
| 2009/0132054 A1* | 5/2009 | Zeegers ............ A61B 17/0642 623/17.16 |
| 2009/0143859 A1 | 6/2009 | McClellan, III |
| 2009/0164020 A1* | 6/2009 | Janowski ............ A61F 2/4465 623/17.16 |
| 2009/0182428 A1 | 7/2009 | McClellan, III et al. |
| 2009/0182430 A1 | 7/2009 | Tyber |
| 2009/0192549 A1 | 7/2009 | Sanders |
| 2009/0192613 A1 | 7/2009 | Wing |
| 2009/0192615 A1 | 7/2009 | Tyber |
| 2009/0192616 A1 | 7/2009 | Zielinski |
| 2009/0198245 A1 | 8/2009 | Phan |
| 2009/0198287 A1 | 8/2009 | Chiu |
| 2009/0198339 A1 | 8/2009 | Kleiner et al. |
| 2009/0210062 A1 | 8/2009 | Thalgott |
| 2009/0210064 A1 | 8/2009 | Lechmann |
| 2009/0224023 A1 | 9/2009 | Moskowitz |
| 2009/0234364 A1 | 9/2009 | Crook |
| 2009/0240333 A1 | 9/2009 | Trudeau et al. |
| 2009/0248092 A1 | 10/2009 | Bellas |
| 2009/0259316 A1 | 10/2009 | Ginn |
| 2009/0265007 A1 | 10/2009 | Colleran |
| 2009/0270873 A1 | 10/2009 | Fabian |
| 2009/0287251 A1 | 11/2009 | Bae |
| 2009/0306779 A1 | 12/2009 | Ahn |
| 2009/0326543 A1 | 12/2009 | Fabian |
| 2009/0326580 A1 | 12/2009 | Anderson |
| 2009/0326589 A1 | 12/2009 | Lemoine |
| 2010/0004747 A1* | 1/2010 | Lin ............... A61B 17/7059 623/17.16 |
| 2010/0016901 A1 | 1/2010 | Robinson |
| 2010/0016973 A1 | 1/2010 | De Villiers et al. |
| 2010/0023128 A1 | 1/2010 | Malberg |
| 2010/0024779 A1 | 2/2010 | Makita |
| 2010/0030334 A1 | 2/2010 | Molz, IV |
| 2010/0036496 A1* | 2/2010 | Yu ............... A61F 2/4425 623/17.14 |
| 2010/0042159 A1 | 2/2010 | Butler |
| 2010/0057206 A1 | 3/2010 | Duffield |
| 2010/0069969 A1 | 3/2010 | Ampuero |
| 2010/0070036 A1 | 3/2010 | Implicito |
| 2010/0070037 A1 | 3/2010 | Parry et al. |
| 2010/0087925 A1 | 4/2010 | Kostuik |
| 2010/0106249 A1 | 4/2010 | Tyber |

(56) References Cited

U.S. PATENT DOCUMENTS

| | | |
|---|---|---|
| 2010/0125334 A1 | 5/2010 | Krueger |
| 2010/0137987 A1 | 6/2010 | Diao |
| 2010/0145457 A1 | 6/2010 | Felt |
| 2010/0145459 A1 | 6/2010 | McDonagh |
| 2010/0145460 A1 | 6/2010 | McDonough |
| 2010/0179656 A1 | 7/2010 | Theofilos |
| 2010/0185287 A1 | 7/2010 | Allard et al. |
| 2010/0185289 A1* | 7/2010 | Kirwan ............... A61F 2/4455 623/17.11 |
| 2010/0191334 A1 | 7/2010 | Keller |
| 2010/0204739 A1 | 8/2010 | Bae et al. |
| 2010/0204796 A1 | 8/2010 | Bae |
| 2010/0217325 A1 | 8/2010 | Hochschuler et al. |
| 2010/0217393 A1 | 8/2010 | Theofilos |
| 2010/0241231 A1 | 9/2010 | Marino et al. |
| 2010/0249935 A1 | 9/2010 | Slivka |
| 2010/0249937 A1 | 9/2010 | Blain et al. |
| 2010/0256759 A1 | 10/2010 | Hansell |
| 2010/0256760 A1 | 10/2010 | Hansell |
| 2010/0268338 A1 | 10/2010 | Melkent et al. |
| 2010/0286777 A1 | 11/2010 | Errico |
| 2010/0286781 A1 | 11/2010 | Bullard |
| 2010/0286783 A1 | 11/2010 | Lechmann |
| 2010/0292696 A1 | 11/2010 | Chantelot |
| 2010/0292737 A1 | 11/2010 | Suh |
| 2010/0305704 A1* | 12/2010 | Messerli et al. ............ 623/17.16 |
| 2010/0312345 A1 | 12/2010 | Duffield |
| 2010/0312346 A1 | 12/2010 | Kueenzi |
| 2010/0324683 A1 | 12/2010 | Reichen et al. |
| 2011/0009908 A1 | 1/2011 | Ferguson |
| 2011/0009966 A1 | 1/2011 | Michelson |
| 2011/0015675 A1 | 1/2011 | Howard |
| 2011/0015745 A1 | 1/2011 | Bucci |
| 2011/0082550 A1 | 4/2011 | Yeh |
| 2011/0082555 A1 | 4/2011 | Martz |
| 2011/0098747 A1 | 4/2011 | Donner |
| 2011/0106159 A1 | 5/2011 | Nazeck |
| 2011/0118840 A1* | 5/2011 | Huntsman ............. A61F 2/4455 623/17.11 |
| 2011/0144703 A1 | 6/2011 | Krause |
| 2011/0160866 A1* | 6/2011 | Laurence ........... A61B 17/1671 623/17.16 |
| 2011/0166656 A1 | 7/2011 | Thalgott et al. |
| 2011/0184415 A1 | 7/2011 | Anderson |
| 2011/0185292 A1 | 7/2011 | Chawla et al. |
| 2011/0190892 A1 | 8/2011 | Kirschman |
| 2011/0202136 A1 | 8/2011 | Brittan |
| 2011/0208311 A1 | 8/2011 | Janowski |
| 2011/0213421 A1 | 9/2011 | Binder et al. |
| 2011/0230970 A1 | 9/2011 | Lynn et al. |
| 2011/0230971 A1* | 9/2011 | Donner ................ A61B 17/70 623/17.16 |
| 2011/0251689 A1 | 10/2011 | Seifert |
| 2011/0276142 A1 | 11/2011 | Niemiec et al. |
| 2011/0282453 A1 | 11/2011 | Greenhalgh |
| 2011/0295371 A1 | 12/2011 | Moskowitz |
| 2011/0319896 A1 | 12/2011 | Papenfuss |
| 2011/0319898 A1 | 12/2011 | O'Neil |
| 2011/0319943 A1 | 12/2011 | Donahoe et al. |
| 2011/0319998 A1 | 12/2011 | O'Neil |
| 2012/0041559 A1 | 2/2012 | Melkent |
| 2012/0078371 A1 | 3/2012 | Gamache |
| 2012/0078372 A1 | 3/2012 | Gamache |
| 2012/0078373 A1* | 3/2012 | Gamache ........... A61B 17/8625 623/17.16 |
| 2012/0083887 A1 | 4/2012 | Purcell et al. |
| 2012/0083889 A1 | 4/2012 | Purcell et al. |
| 2012/0143336 A1 | 6/2012 | Aflatoon et al. |
| 2012/0150301 A1 | 6/2012 | Gamache |
| 2012/0150303 A1 | 6/2012 | Linares |
| 2012/0158143 A1 | 6/2012 | Shapiro |
| 2012/0191190 A1 | 7/2012 | Trieu |
| 2012/0191204 A1 | 7/2012 | Bae et al. |
| 2012/0197401 A1 | 8/2012 | Duncan |
| 2012/0203230 A1 | 8/2012 | Adams |
| 2012/0209331 A1 | 8/2012 | Michelson |
| 2012/0215315 A1 | 8/2012 | Hochschuler et al. |
| 2012/0226319 A1 | 9/2012 | Armstrong |
| 2012/0253406 A1 | 10/2012 | Bae |
| 2013/0041471 A1 | 2/2013 | Siegal |
| 2013/0060337 A1 | 3/2013 | Petersheim |
| 2013/0073044 A1 | 3/2013 | Gamache |
| 2013/0079883 A1 | 3/2013 | Butler |
| 2013/0103102 A1 | 4/2013 | Taylor et al. |
| 2013/0144391 A1 | 6/2013 | Siegal et al. |
| 2013/0166027 A1 | 6/2013 | Bellas |
| 2013/0238095 A1 | 9/2013 | Pavento |
| 2013/0261747 A1 | 10/2013 | Geisert |
| 2013/0268080 A1 | 10/2013 | Melkent |
| 2013/0310939 A1 | 11/2013 | Fabian |
| 2013/0325071 A1 | 12/2013 | Niemiec |
| 2013/0345813 A1 | 12/2013 | Frank |
| 2014/0039623 A1 | 2/2014 | Iott |
| 2014/0067069 A1 | 3/2014 | Lopez |
| 2014/0094916 A1 | 4/2014 | Glerum |
| 2014/0107786 A1 | 4/2014 | Geisler |
| 2014/0114415 A1 | 4/2014 | Tyber |
| 2014/0135930 A1 | 5/2014 | Georges |
| 2014/0142705 A1 | 5/2014 | Duffield |
| 2014/0156009 A1 | 6/2014 | Armstrong |
| 2014/0172103 A1 | 6/2014 | O'Neil |
| 2014/0277507 A1 | 9/2014 | Baynham |
| 2014/0296983 A1 | 10/2014 | Fauth et al. |
| 2014/0336771 A1 | 11/2014 | Zambiasi et al. |
| 2014/0364917 A1 | 12/2014 | Sandstrom |
| 2015/0112437 A1 | 4/2015 | Davis et al. |
| 2015/0230929 A1 | 8/2015 | Lorio |
| 2015/0297356 A1 | 10/2015 | Gamache |
| 2015/0313721 A1 | 11/2015 | Gamache |
| 2015/0374511 A1 | 12/2015 | Pavento |
| 2016/0045325 A1 | 2/2016 | Bellas et al. |
| 2016/0051373 A1 | 2/2016 | Faulhaber |
| 2016/0051374 A1 | 2/2016 | Faulhaber |
| 2016/0067052 A1 | 3/2016 | Cain et al. |
| 2016/0128846 A1 | 5/2016 | Voellmicke |
| 2016/0199195 A1 | 7/2016 | Hauck et al. |
| 2016/0213487 A1 | 7/2016 | Wilson |
| 2016/0296342 A1 | 10/2016 | Woods |
| 2016/0317317 A1 | 11/2016 | Marchek et al. |
| 2016/0324660 A1 | 11/2016 | Pavento |
| 2016/0324662 A1 | 11/2016 | McDonough et al. |
| 2017/0056179 A1 | 3/2017 | Lorio |
| 2017/0065427 A1 | 3/2017 | Songer |
| 2017/0071756 A1 | 3/2017 | Slivka et al. |
| 2017/0095341 A1 | 4/2017 | Smith |
| 2017/0100177 A1 | 4/2017 | Kim |
| 2017/0224493 A1 | 8/2017 | Pavento |
| 2017/0304068 A1 | 10/2017 | Bellas |
| 2017/0312090 A1 | 11/2017 | Sharabani |
| 2018/0125672 A1 | 5/2018 | Pavento |
| 2018/0256362 A1 | 9/2018 | Slivka et al. |
| 2018/0318101 A1 | 11/2018 | Engstrom |
| 2019/0008654 A1 | 1/2019 | Thommen |
| 2019/0133785 A1 | 5/2019 | Georges |
| 2019/0133786 A1 | 5/2019 | Voellmicke |
| 2019/0269522 A1 | 9/2019 | Pavento et al. |
| 2020/0008958 A1 | 1/2020 | Gamache et al. |
| 2020/0078192 A1 | 3/2020 | Marchek et al. |
| 2020/0121473 A1 | 4/2020 | Gamache et al. |

FOREIGN PATENT DOCUMENTS

| | | |
|---|---|---|
| DE | 19710392 | 7/1999 |
| EP | 1121906 | 8/2001 |
| EP | 1609444 | 12/2005 |
| EP | 1683490 | 7/2006 |
| EP | 1774926 | 4/2007 |
| EP | 1459711 | 7/2007 |
| EP | 1847240 | 10/2007 |
| EP | 1506753 | 9/2009 |
| EP | 2156812 | 2/2010 |
| FR | 2634260 | 1/1990 |
| FR | 2894130 | 6/2007 |

(56) References Cited

FOREIGN PATENT DOCUMENTS

| | | |
|---|---|---|
| GB | 457673 | 12/1936 |
| GB | 2220729 | 1/1990 |
| GB | 2457673 | 8/2009 |
| JP | 2005-524472 | 8/2005 |
| JP | 2006-524114 | 10/2006 |
| JP | 2007-516808 | 6/2007 |
| JP | 2008-514362 | 5/2008 |
| JP | 2012508044 | 4/2012 |
| JP | 2013516206 | 5/2013 |
| WO | WO 1998004217 | 2/1998 |
| WO | WO 1998/034568 | 8/1998 |
| WO | WO 1999038463 | 8/1999 |
| WO | WO 1999052473 | 10/1999 |
| WO | WO 2001008864 | 2/2001 |
| WO | WO 2002013732 | 2/2002 |
| WO | WO 2003/003951 | 1/2003 |
| WO | WO 2003/005938 | 1/2003 |
| WO | WO 2003005939 | 1/2003 |
| WO | WO 03/047473 | 6/2003 |
| WO | WO 2003070128 | 8/2003 |
| WO | WO 2003090650 | 11/2003 |
| WO | WO 2004069106 | 8/2004 |
| WO | WO 2005020861 | 3/2005 |
| WO | WO 2006084057 | 8/2006 |
| WO | WO 2006/058281 | 10/2006 |
| WO | WO 2007003785 | 1/2007 |
| WO | WO 2007098288 | 8/2007 |
| WO | WO 2007118856 | 10/2007 |
| WO | WO 2008149223 | 12/2008 |
| WO | WO 2009/025841 | 2/2009 |
| WO | WO 2009064644 | 5/2009 |
| WO | WO 2009091775 | 9/2009 |
| WO | WO 2009/136009 | 11/2009 |
| WO | WO 2010028045 | 3/2010 |
| WO | WO-2010028045 A1 * 3/2010 ......... A61B 17/1671 |  |
| WO | WO 2010033786 | 3/2010 |
| WO | WO 2010/054181 | 5/2010 |
| WO | WO 2010054208 | 5/2010 |
| WO | WO 2010092893 | 9/2010 |
| WO | WO 2010099239 | 9/2010 |
| WO | WO 2010125514 | 11/2010 |
| WO | WO 2010121028 | 12/2010 |
| WO | WO 2011/008864 | 1/2011 |
| WO | WO 2011/035126 | 3/2011 |
| WO | WO 2011/080535 | 7/2011 |
| WO | WO 2012/047712 | 4/2012 |
| WO | WO 2012/056119 | 5/2012 |
| WO | WO 2013018062 | 2/2013 |
| WO | WO 2013/062716 | 5/2013 |
| WO | WO 2013/096192 | 6/2013 |
| WO | WO 2013/191979 | 12/2013 |

OTHER PUBLICATIONS

Cain, "New Stand-Alone Anterior Lumbar Interbody Fusion Device: Bioemechanical Comparison with Established Fixation Techniques", Spine, vol. 30, No. 23, pp. 2631-2636, 2005, Lippincott Williams & Wilkins Inc.

Cohn and Younes, "Biodegradable PEO/PLA Block Copolymers", Journal of Biomaterials Research, 1988, vol. 22, pp. 993-1009.

Cohn, "Polymer Preprints", ACS Division of Polymer Chemistry, vol. 30(1), 1989, p. 498, (e.g. PEO/PLA).

Gercek, "Subsidence of Stand-Alone Cervical Cages in Anterior Interbody Fusion: Warning", Eur Spine J., vol. 12, pp. 513-516, 2003, Springer-Verlag.

Heller, "Poly(Ortho Esters)", Handbook of Biodegradable Polymers, edited by Domb, etal, Hardwood Academic Press, pp. 99-118, 1997.

Humphries, "Anterior Fusion of the Lumbar Spine Using an Internal Fixative Device", Surgical Forum, vol. IX, pp. 770-773, American College of Surgeons, 1959, Chicago Illinois.

Kandziora, "Biomechanical Comparison of Cervical Spine Interbody Fusion Cages", Spine, vol. 26, No. 17, pp. 1850-1857, 2001, Lippincott Williams & Wilkins, Inc.

Kemnitzer and Kohn, "Degradable Polymers Derived From The Amino Acid L-Tyrosine", The Handbook of Biodegradable Polymers, edited by Domb, et al., Hardwood Academic Press, 1997, pp. 251-272.

Oxland, "A Comparative Biomechanical Investigation of Anterior Lumbar Interbody Cages: Central and Bilateral Approaches", The Journal of Bone and Joint Surgery, pp. 383-393, vol. 82A, No. 3, Mar. 2000.

Pavlov, "Good Outcome and Restoration of Lordosis After Anterior Lumbar Interbody Fusion With Additional Posterior Fixation", Spine, vol. 29, No. 17, pp. 1893-1899, 2004, Lippincott Williams & Wilkins.

Samandouras, "A New Anterior Cervical Instrumentation System Combining an Intradiscal Cage With an Integrated Plate", Spine, vol. 26, No. 10, pp. 1188-1192, 2001, Lippincott Williams and Watkins, Inc.

Vandorpe, "Biodegradable Polyphosphazenes For Biomeideal Applications", The Handbook of Biodegradable Polymers, edited by Domb, et al., Hardwood Academic Press, 1997, pp. 161-182.

Pederson, "Thermal Assembly of a Biomimetic Mineral/Collagen Composite", Biomaterials, 2003, vol. 2, pp. 4881-4890, Elsevier.

U.S. Appl. No. 13/673,061, filed Nov. 6, 2012, Bacem.

Schmiedberg, Isolation and characterization of metallic wear debris from a dynamic intervertebral disc prosthesis, J. Biomed. Mater. Res., vol. 28 Issue 11, 1277-1288, Nov. 1994.

\* cited by examiner

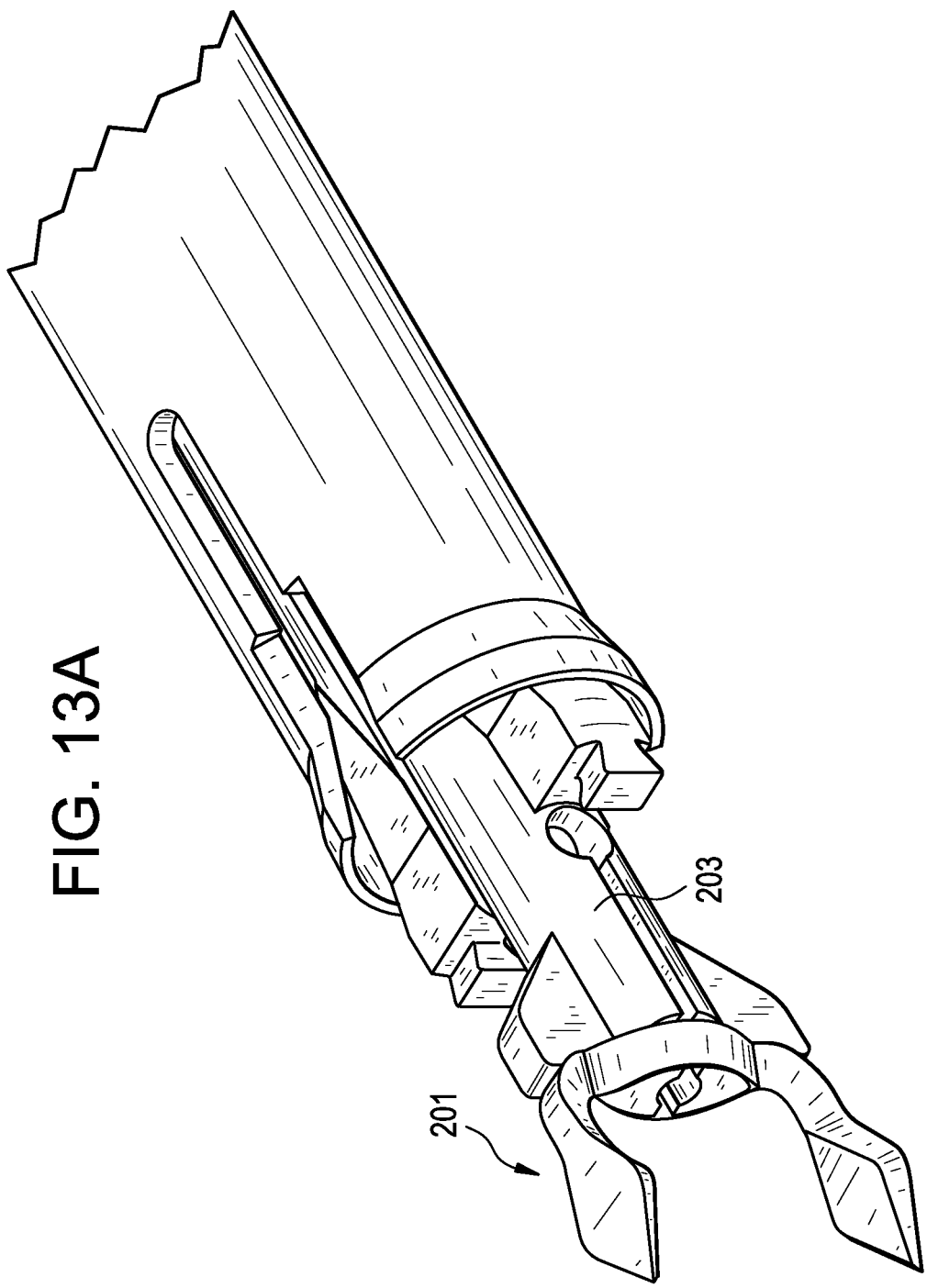

FUSION CAGE WITH IN-LINE SINGLE PIECE FIXATION

RELATED APPLICATIONS

This application claims priority from U.S. Ser. No. 61/385,959, filed on Sep. 23, 2010, and entitled "Stand Alone Intervertebral Fusion Device", and is related to non-provisional U.S. Ser. No. 13/237,233, filed on even date, entitled "Stand Alone Intervertebral Fusion Device", the specifications of which are incorporated by reference in their entireties.

This application claims priority from U.S. Ser. No. 61/466,309, filed on Mar. 22, 2011, and entitled "Novel Implant Inserter Having a Laterally-Extending Dovetail Engagement Feature", and is related to non-provisional U.S. Ser. No. 13/237,200, filed on even date, entitled "Novel Implant Inserter Having a Laterally-Extending Dovetail Engagement Feature", the specifications of which are incorporated by reference in their entireties.

This application claims priority from U.S. Ser. No. 61/466,321, filed on Mar. 22, 2011, and entitled "Fusion Cage with In-Line Single Piece Fixation", the specification of which is incorporated by reference in its entirety.

BACKGROUND OF THE INVENTION

Spine surgeons have articulated a desire not to insert a plate on the anterior surface of a vertebral body and then place fixation devices such as bone screws through that plate. Often times, the plate may be considered to be too proud and its profile can sometimes cause patient discomfort and may be related to dysphasia.

PCT Published Patent Application WO 02/013732 (Bramlet) discloses an apparatus and method for fusing opposing spinal vertebrae. The implant includes a body assembly and a retention member coupled to the body assembly. The retention member includes a tang where the tang is extendible from the body assembly. The method includes the step of inserting an implant between adjacent vertebrae with a retention member of the implant in a first retracted configuration. The method also includes the step of configuring the retention member in a second extended configuration wherein the retention member is in its second extended configuration, a portion of a tang of the retention member extends from the implant and into at least one of the adjacent vertebrae.

U.S. Pat. No. 6,336,928 (DePuy France) discloses a device for joining at least two vertebral bodies, which comprises at least one plate equipped at each end with anchoring parts which can be introduced substantially vertically into seats previously established in the vertebral bodies to be joined, and then, after introduction, can be folded back at an angle towards one another in order to exert a constant compression of the vertebral bodies and to ensure perfect anchoring, wherein each anchoring part is connected to the ends of the corresponding plate via a central connection zone delimiting two profiled notches in order to permit deformation of the zone, in such a way that each pair of anchoring parts permits a compression, both at the level of the plate and at the level of its ends, and in such a way that the anchoring parts at each end of the plate permit a clamping which prevents any extraction.

U.S. Pat. No. 7,594,931 (LDR I) discloses an intervertebral arthrodesis for insertion in an intervertebral space separating opposite faces of two adjacent vertebrae has a ring shaped intervertebral cage having a bar that extends perpendicular to the axis of the spine. The bar has a height less than the rest of the cage. A surface of the cage contacting the vertebrae has an undulating shape for limiting sliding of the cage in a plane parallel to the vertebrae faces.

PCT Published Patent Application WO2008/149223 (LDR II) discloses an intersomatic cage, an intervertebral prosthesis, an anchoring device and an instrument for implantation of the cage or the prosthesis and the anchoring device, as well as a system and a method for implanting spinal implants and anchoring devices in vertebrae. An intersomatic cage or an intervertebral prosthesis fit closely to the anchoring device, which includes a body of elongated shape on a longitudinal axis, of curved shape describing, along the longitudinal axis, an arc whose dimensions and radius of curvature are designed in such a manner that the anchoring device may be implanted in the vertebral plate of a vertebra by presenting its longitudinal axis substantially along the plane of the intervertebral space, where the anchoring device is inserted, by means of the instrument; through a slot located in at least one peripheral wall of the cage or on at least one plate of the intervertebral disc prosthesis to penetrate into at least one vertebral plate PCT Published Patent Application WO2010/028045 (Synthes) discloses an intervertebral implant for insertion into an intervertebral disc space between adjacent vertebral bodies or between two bone portions. The implant includes a spacer portion, a plate portion operatively coupled to the spacer portion and one or more blades for securing the implant to the adjacent vertebral bodies. The blades preferably include superior and inferior cylindrical pins for engaging the adjacent vertebral bodies. The implant may be configured to be inserted via a direct lateral trans-psoas approach. Alternatively, the implant may be configured for insertion via an anterior approach US Patent Publication No. 2005-0149192 & 2005-0149193 (Zucherman I and II) disclose an intervertebral implant has a fusion body with at least one keel that anchors the implant into cancellous bone of at least one vertebral body. A method for implantation includes lateral implantation of the implant.

US Patent Publication No. 2004-0260286 (Ferree) discloses intradiscal components associated with Total Disc Replacements (TDRs), for example, are maintained in a disc space with keels having attributes that resist extrusion, pull-out, and/or backout. In the preferred embodiment, the keel is curved to resist extrusion, particularly anterior or posterior extrusion. The invention may include a TDR with a pair of endplates, each with a keel extending into a different vertebral body, and wherein the keels are angled or curved in different directions to resist extrusion. In alternative embodiments, the keel may include one or more members that extend outwardly to resist extrusion. Such members may be spring-biased, composed of a shape-memory material, or extend outwardly in response to an applied mechanical force, as might be applied by turning a screw. The keel may further include a bone-ingrowth plug or coating or 'teeth' to resist extrusion. Keels according to the invention may also be configured to resist extrusion through the addition of an elongate member that penetrates a vertebral body and the keel. Such a member may be a secondary keel or screw.

US Patent Publication No. 2008-0167666 (Fiere) discloses equipment including at least one U-shaped clip whose lateral branches have sections and widths such that they may be inserted in the vertebral bodies of two vertebrae by impaction on the intermediate branch of the clip, so as to rest along the cortical bones of the vertebral bodies, and whose intermediate branch is deformable in such a way as to allow a reduction of the distance between the lateral branches; the intermediate branch, before implantation, has a length such that one of the lateral branches may be positioned slightly above the cortical bone forming the plate of the subjacent vertebra while the other lateral branch may be positioned slightly below the cortical bone forming the plate of the subjacent vertebra, and has, after deformation, a length such that the two lateral branches may be brought closer to each other.

U.S. Pat. No. 6,773,437 (Ogilvie) discloses a fusionless method of correcting spinal deformities in growing adolescents, utilizing a shape memory alloy staple. Various embodiments of the shape memory alloy staple include features such as barbs on the inner and outer surfaces of the prongs in the shape memory alloy staple as well as the use of notches on the crossbar or cross plate connecting the prongs to the shape memory alloy staple. In some embodiments, the shape memory alloy staple has an aperture defined through the cross plate for receiving a bone screw or other bone anchor which in turn allows the interconnection of a longitudinal member.

US Patent Publication No. US 2010-0004747 (Lin) discloses a trans-vertebral and intra-vertebral plate and a rectangular cage with a slot for the plate of spinal fixation device are for neutralizing intervertebral movement for the spinal interbody fusion. The rectangular cage with a vertical or oblique slot is inserted into the intervertebral space from the lateral or anterior side of the spinal column and then the plate is inserted through the slot of the cage and hammered into and buried inside two adjacent vertebral bodies, to achieve three-dimensional intervertebral fixation.

US2010-0204739 (Bae) discloses a system for spinal surgery including a prosthesis comprising a plurality of bone anchors which engage an intervertebral construct for fusion or motion preservation. The fusion construct comprises a spacer optionally encircled by a jacket. The motion preservation construct may comprise an articulating disc assembly or an elastomeric disc assembly. Any of the constructs may occupy the intervertebral disc space between adjacent vertebrae after removal of an intervertebral disc. The anchors slidingly engage the construct to securely fix the prosthesis to the vertebrae. The anchors and jacket of the fusion construct provide a continuous load path across opposite sides of the prosthesis so as to resist antagonistic motions of the spine.

SUMMARY OF THE INVENTION

The present invention relates to fixing an intervertebral fusion cage to its adjacent vertebral bodies with a single staple, wherein each tyne of the staple traverses the anterior wall of the cage at an angle so that the staple enters both of the vertebral bodies. The staple is designed to be a zero-profile staple.

Generally, the present invention relates to methods for securing the cage to one or more levels of the spine with fixation. The fixation, which is typically a staple, is intended to be driven perpendicular to the proximal face of the cage, and in-line with the inserter. After the cage is placed and positioned according to surgeon preference, a single piece fixation clip is then deployed and fixed in a manner that produces a zero-profile device.

The staple's shape may be designed to provide compression onto the cage once placed in its desired location.

The device of the present invention allows for a smaller incision and access site, and the in-line nature of the staple also frees the surgeon from having to insert the staple at a high angle through sometimes challenging approaches.

Therefore, the present invention is advantageous because it allows for fixation of the cage to each of the vertebral bodies via a single staple. The staple is preferably designed to provide an essentially zero-profile device. This staple may be inserted fully through or partially through a side wall of the cage and into the adjacent vertebral bodies. Further, these staples may be designed to provide compression to the graft held within the cage and thereby promote fusion.

In certain embodiments, the staple is designed to be tapped flush to the vertebral body. The staple may also provide compression onto the graft using a shape memory or spring material. In certain embodiments, the staple may allow for independent cage insertion and staple insertion, with the option to either insert the staple in-line with the cage or to disengage the staple from the cage and place it anywhere about the cage.

DESCRIPTION OF THE FIGURES

FIG. 4b discloses the inserter of FIG. 4a.

FIG. 6b discloses a magnified view of the distal end of FIG. 6a.

FIGS. 13a-d disclose steps in one method of inserting the device of the present invention.

DETAILED DESCRIPTION OF THE INVENTION

Figure 1A:
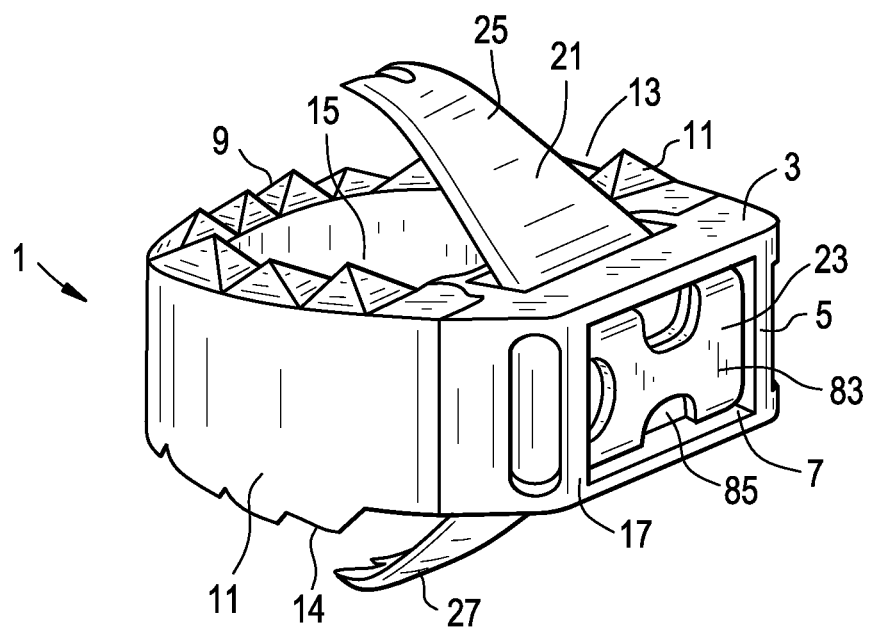
FIG. 1a discloses a perspective view of a zero profile device of the present invention.
Figure 1B:
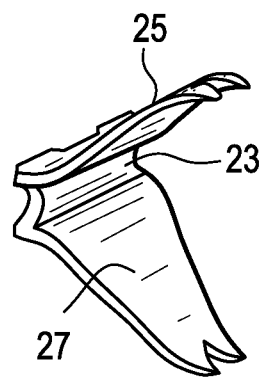
FIG. 1b discloses a staple of the present invention.

Now referring to FIGS. 1a and 1b, there is provided (claim 1) a zero-profile intervertebral fusion device comprising:

a) an intervertebral fusion cage 1 comprising an anterior wall 3 having an anterior face 5 having a recess 7 therein, a posterior wall 9, a pair of side walls 11 connecting the anterior and posterior walls, an upper surface 13, a lower surface 14, and a through hole 15 extending from the upper surface to the lower surface, the cage having an anterior end 17, b) a staple 21 comprising a first crossbar 23 and first 25 and second 27 tynes extending therefrom, wherein at least a portion of the first crossbar of the staple is disposed in the recess in the anterior face of the anterior wall, and wherein the first tyne extends above the upper surface of the cage and the second tyne extends below the bottom surface of the cage, wherein the anterior face is the anterior end of the cage.

Figure 2:
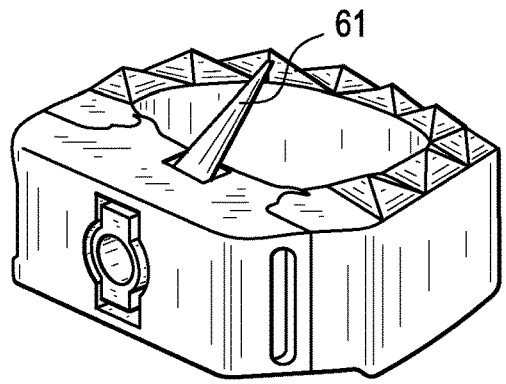
FIG. 2 discloses a device of the present invention having a staple having a pair of sharp tips.

This cage of FIG. 1 differs from that of Bramlet (FIGS. 1 and 2) in that the cage of the present invention is zero profile (whereas the cap of Bramlet projects out from the cage wall).

Figure 5A:
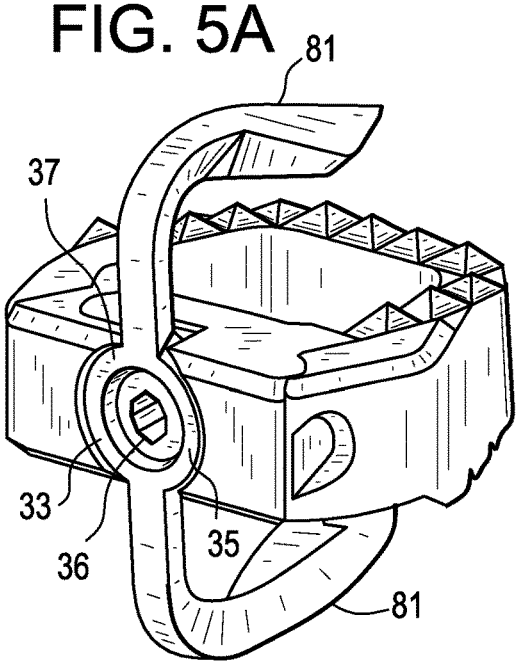
FIG. 5a discloses a device of the present invention having a staple wherein each tyne has an enlarged head.
Figure 5B:
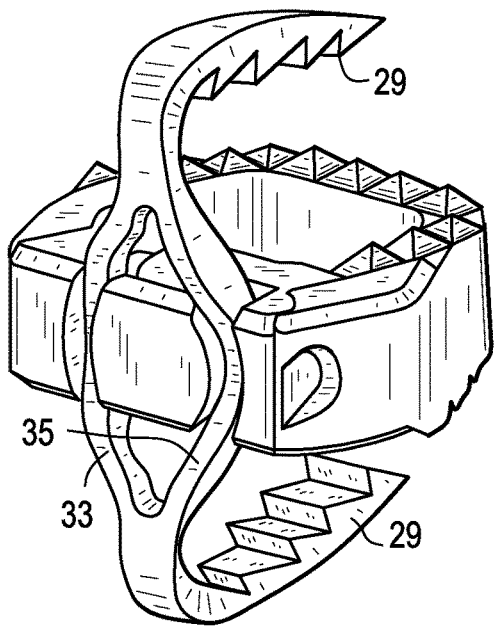
FIG. 5b discloses a device of the present invention having a staple wherein each tyne has a plurality of teeth.
Figure 9:
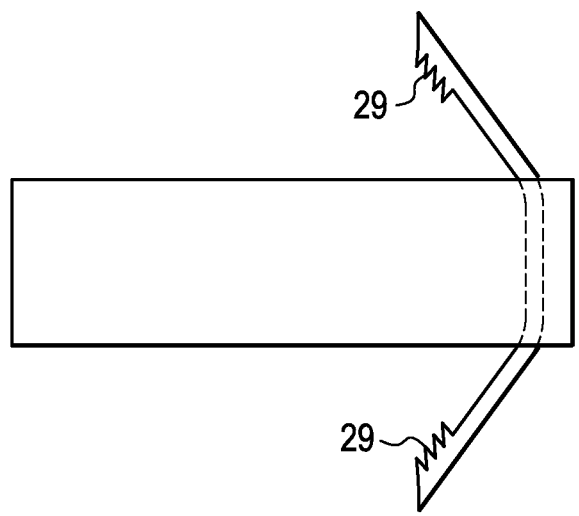
FIG. 9 discloses a device of the present invention having a staple wherein each tyne has a plurality of teeth.

In some embodiments (as in FIGS. 5b and 9), each tyne of the staple comprises a plurality of teeth 29. These teeth further augment the fixation quality of the staple that secures the cage to the opposing vertebral bodies.

Figure 8A:
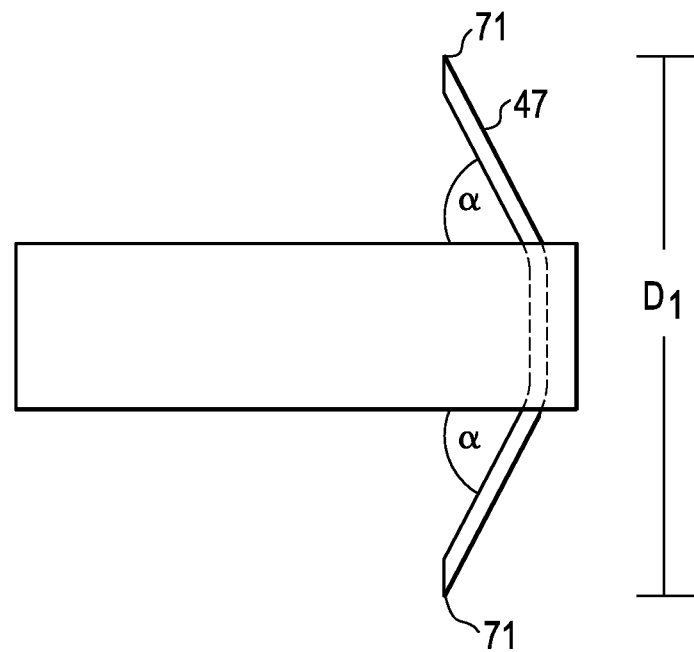
FIGS. 8a and 8b disclose a side view of the same device of the present invention in which the staple has a first and a second configuration.
Figure 8B:
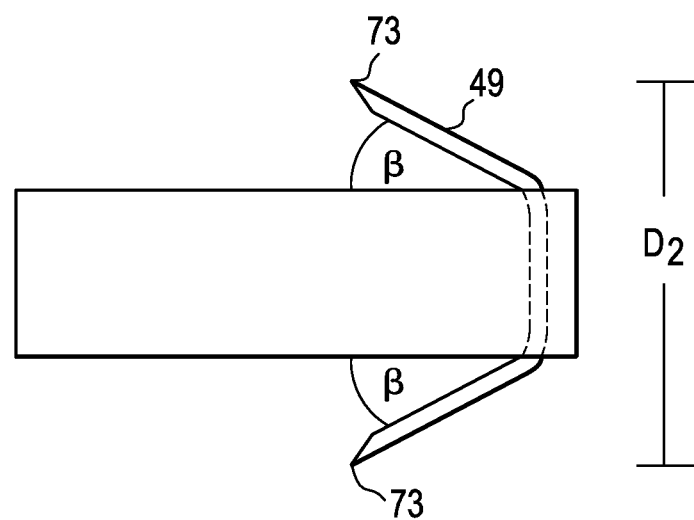

In some embodiments (as in FIGS. 8a and 8b), the staple comprises a shape memory material. This feature allows the staple to reconfigure itself upon warming (or upon removal of stress) to compress the regions directly above, below and through the cage, thereby promoting fusion through the cage.

Figure 3:
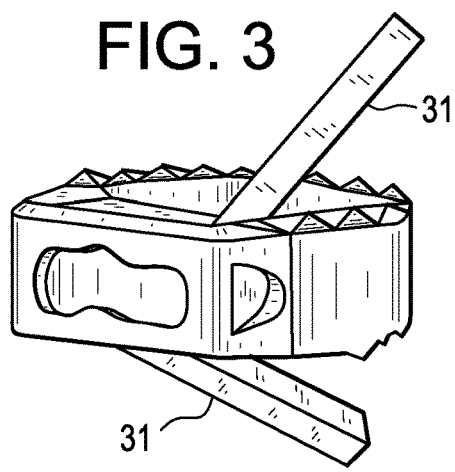
FIG. 3 discloses a device of the present invention having a staple having skewed tynes.

In some embodiments (as in FIG. 3), the tynes 31 are disposed in a skewed orientation. The skewed nature of the tynes discourages their simultaneous backout from the vertebral bodies. The skewed nature may be produced by materials properties, by cage geometry, by manipulation by an instrument, by adding a component, or by recess geometry.

In some embodiments, at least one tyne extends from the first crossbar at an obtuse angle from the first crossbar. This orientation allows the tyne to extend above the cage and into the adjacent vertebral body.

In some embodiments, the staple comprises at least two crossbars 33, 35. The use of two crossbars allows a passageway to be formed therbetween (as in FIGS. 5a and 5b). A set screw 36 may be inserted into this passageway so as to provide security of the staple.

In some embodiments, (as in FIG. 5a) the two cross bars substantially form an annulus 35. The annular passageway of this embodiment is advantageous to the use of the set screw described above.

In some embodiments (as in FIG. 5a) the set screw 36 passes through the annulus and fully into the recess in the anterior face of the anterior wall. This produces the zero profile characteristic desirable in cervical cages.

In some embodiments (as in FIG. 3), at least one tyne 31 extends from the first crossbar at an obtuse angle from the anterior wall. This quality allows the tyne to penetrate deep into the opposing vertebral bodies.

Still referring to FIG. 1a and FIG. 1b, there is provided (claim 10) a two-piece intervertebral fusion device consisting of:

a) an intervertebral fusion cage comprising an anterior wall having an anterior face having a recess therein, a posterior wall, a pair of side walls connecting the anterior and posterior walls, an upper surface, a lower surface, and a through hole extending from the upper surface to the lower surface, b) an integral staple comprising a first crossbar and first and second tynes extending therefrom, wherein at least a portion of the first crossbar of the staple is disposed in the recess in the anterior face of the anterior wall, and wherein the first tyne extends above the upper surface of the cage and the second tyne extends below the bottom surface of the cage.

This cage of FIG. 1a further differs from that of Bramlet (FIGS. 1 and 2) in that the cage of the present invention has no compression cap (whereas Bramlet requires a compression cap to secure the staple).

Thus, (as in FIG. 1a) in some embodiments (claim 35), the intervertebral fusion device consists of the cage and the staple.

Figure 7A:
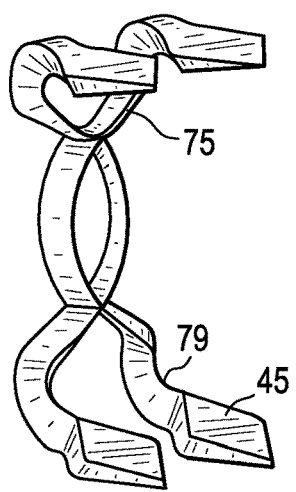
FIG. 7a discloses a staple of the present invention having two tynes extending from each end of its crossbar.
Figure 7B:
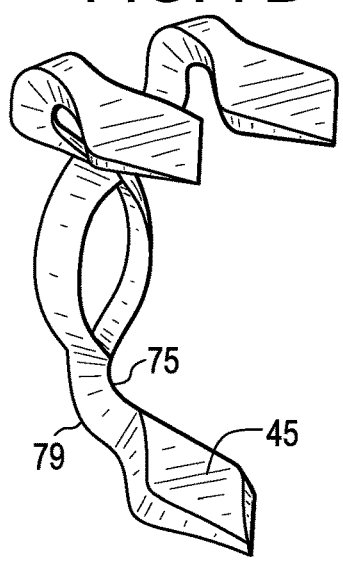
FIG. 7b discloses a staple of the present invention having two tynes extending from a first end of its crossbar, and one tyne extending from the second end of the crossbar.

In some embodiments (as in FIGS. 7a and 7b), at least one tyne 45 has a width and a height, wherein the width of the tyne is at least two times the height. The wide nature of this tyne provides further security to the fixation quality of the staple, thereby enhancing the fixation of the cage to the vertebral bodies.

In some embodiments (claim 24) (as in FIGS. 8a and 8b), the staple comprises a shape memory material and has a martensitic configuration 47 and an austenitic configuration 49, wherein at least one tyne forms a first angle $\alpha$ with the crossbar in the martensitic configuration and a second angle $\beta$ with the crossbar in the austenitic configuration. This quality allows the staple to reconfigure itself upon warming to compress the regions directly above, below and through the cage, thereby promoting fusion through the cage.

In some shape memory embodiments (as in FIGS. 8a and 8b), the first angle $\alpha$ is greater than the second angle. This promotes the desirable compression of the bone graft discussed above.

In some embodiments, the device further comprises a bone graft material disposed within the throughhole. This bone graft enhances the possibilities of providing bony fusion through the cage.

In some embodiments thereof, the staple provides compression of the bone graft material. Compression of the bone graft enhances the possibilities of providing bony fusion through the cage.

Figure 10:
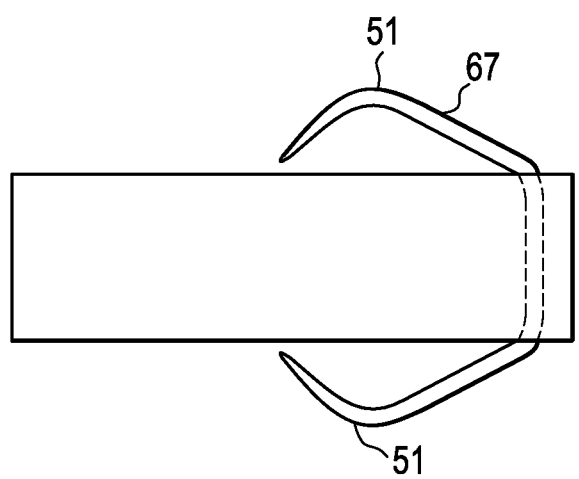
FIG. 10 discloses a device of the present invention in which the tynes of the staple curve back towards to the cage.

In some embodiments (as in FIG. 10), each tyne has a distal end portion 51 that curves inward. These inwardly curving tynes can provide compression of the bone graft disposed in the cage, thereby enhancing the possibilities of providing bony fusion through the cage.

In some embodiments (as in FIG. 5b), the recess in the anterior wall extends from the upper surface to the lower surface of the cage. The feature allows the staple to be fully seated in the anterior wall, thereby providing a zero profile device. In particular, each tyne thereof is disposed fully posterior to the anterior face of the anterior wall.

In some embodiments (as in FIGS. 5a and 5b), the staple extends through the upper surface of the cage and through the bottom surface of the cage. This allows the staple to enter the vertebral bodies at a high elevation while providing the desirable zero profile quality.

Figure 14:
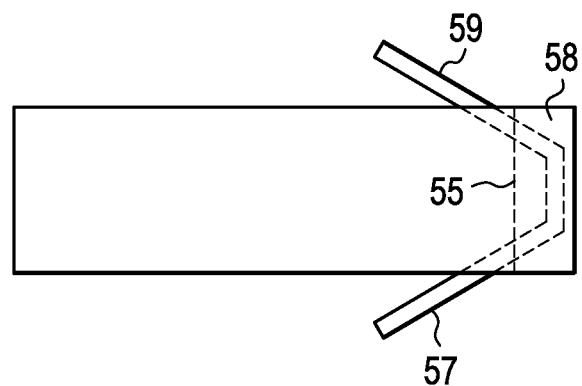
FIG. 14 discloses an implant of the present invention in which the tynes extend through the posterior face of the anterior wall.
Figure 12A:
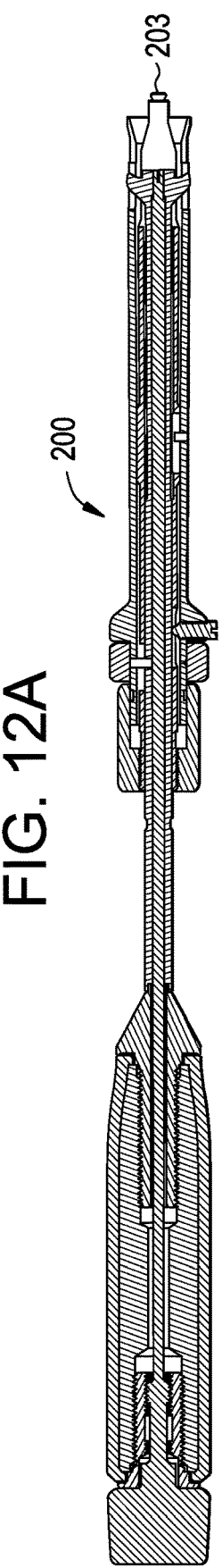
FIGS. 12a-12d disclose various side and cross-sectional views of an inserter for devices of the present invention.
Figure 12B:
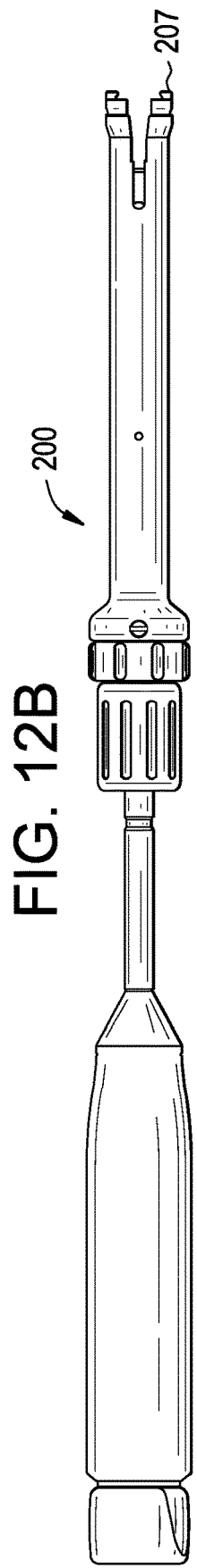
Figure 12C:
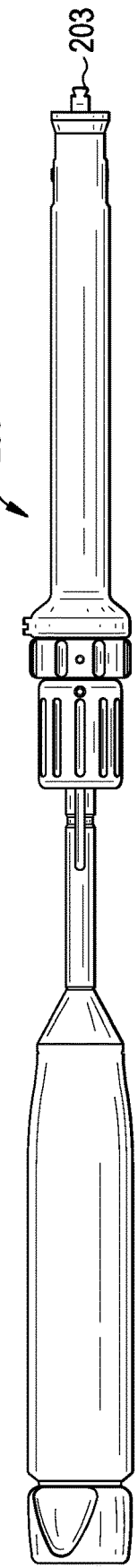
Figure 12D:
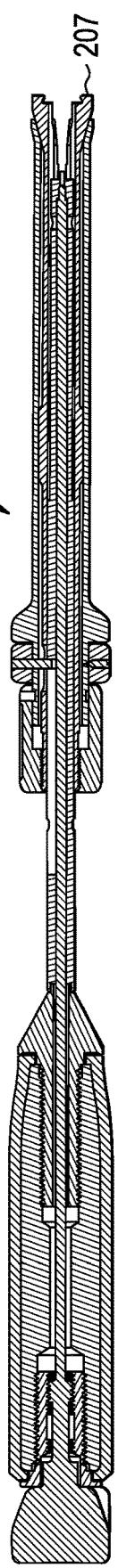

In some embodiments (as in FIG. 14), the anterior wall 58 of the cage has a posterior face 55, and the first 57 and second 59 tynes extend through the posterior face of the anterior wall. This embodiment ensures that the tynes penetrate the opposed vertebral bodies further towards the central region of the vertebral endplates, thereby providing a more balanced fixation of the cages to the vertebral bodies.

In some embodiments (as in FIG. 3), the recess defines an upper hole extending through the anterior wall and a lower hole extending through the anterior wall, and the tynes extend through the upper and lower holes.

In some embodiments (as in FIG. 2), the tynes extend to a sharp distal tip 61. This sharp tip assists in penetrating the opposed vertebral bodies during staple insertion.

Figure 11:
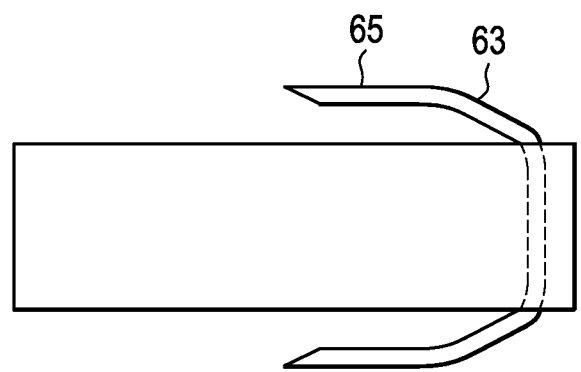
FIG. 11 discloses a device of the present invention in which the tynes of the staple curve so that the distal ends thereof run substantially parallel to the cage.

In some embodiments (as in FIG. 11), a proximal portion 63 of the first tyne extends in a first direction and a distal portion 65 of the first tyne extends in a second direction, the second direction being more parallel to the upper surface of the cage than the first direction.

In some embodiments (as in FIG. 10), a proximal portion 67 of the first tyne extends away from the cage and a distal portion 51 of the first tyne extends towards the cage.

In some embodiments (as in FIGS. 8a and 8b), the distal ends 71 of the tynes in the first configuration are separated by a first distance $D_1$, and the distal ends 73 of the tynes in the second configuration are separated by a second distance $D_2$, and the second distance $D_2$ is less than the first distance $D_1$.

In some embodiments (as in FIG. 5a), both the set screw and the intermediate portion of the first crossbar of the staple are fully disposed in the recess in the anterior face of the anterior wall.

In some embodiments, (as in FIGS. 7a and 7b), the posterior face 75 of the crossbar forms a sharp blade.

In some embodiments (as in FIGS. 5a, 7a and 7b), the distal portion of each tyne 79 forms an enlarged head 81.

In some embodiments (as in FIG. 1a), the crossbar of the staple comprises an anterior face 83 having a recess 85 therein adapted for coupling to an inserter instrument.

In some embodiments (as in FIG. 1a), the cage has at least one recess, wherein the second configuration is dictated by recess geometry or a cover plate Now referring to FIGS. 12a-12d, there are provided various side and cross-sectional views of an inserter 200 for devices of the present invention. The inserter includes an outer cannula, an outer grabber having a pair of distal prongs; an inner grabber tip having a single distal head, a proximal knob that actuates the inner grabber tip; an intermediate knob that selectively deploys either the staple or the cage, and a distal knob that actuates the outer grabber tip. The outer grabber tip is adapted to hold and insert the cage of the present invention. The inner grabber tip is adapted to hold and inserter the staple of the present invention.

Figure 4A:
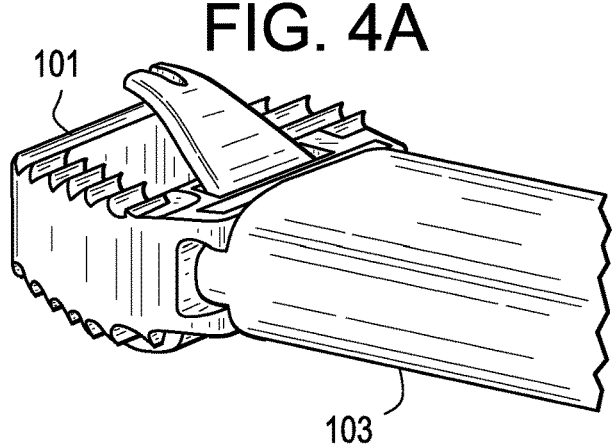
FIG. 4a discloses an inserter of the present invention having a device of the present invention mounted thereon.
Figure 4B:
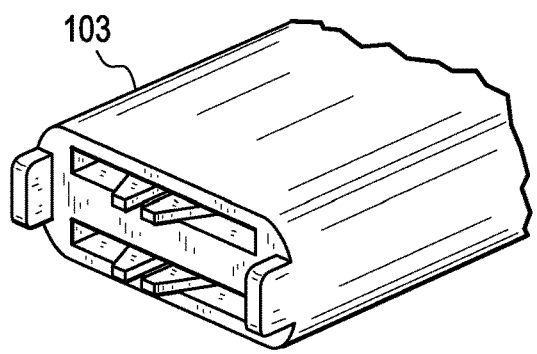
Figure 6A:
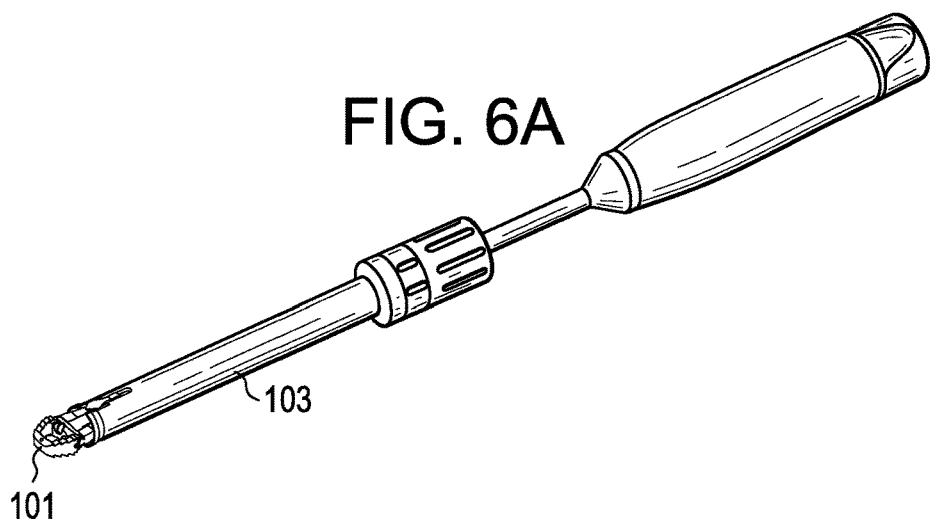
FIG. 6a discloses an inserter of the present invention having a device of the present invention mounted thereon.
Figure 6B:
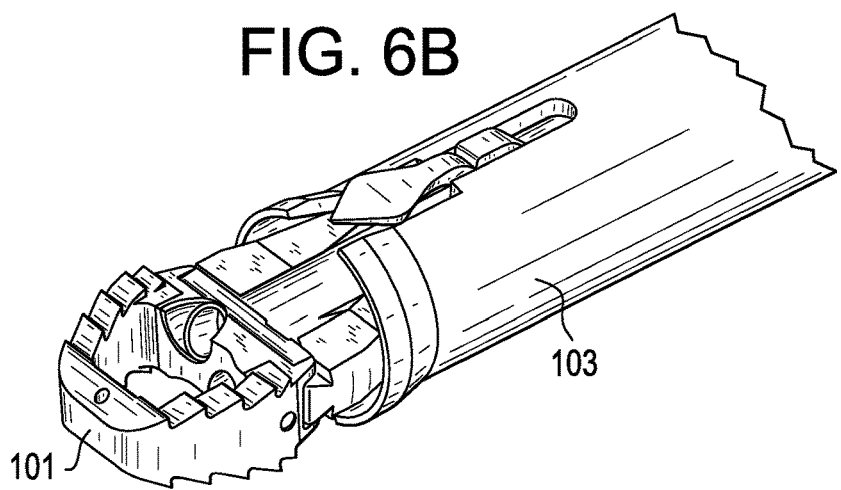

Other views of assemblies of the present invention in which a cage 101 is mounted on the inserter 103 are shown in FIGS. 4a, 6a and 6b. View of one style of inserter 103 that can be used with the present invention is shown in FIG. 4b.

Figure 13B:
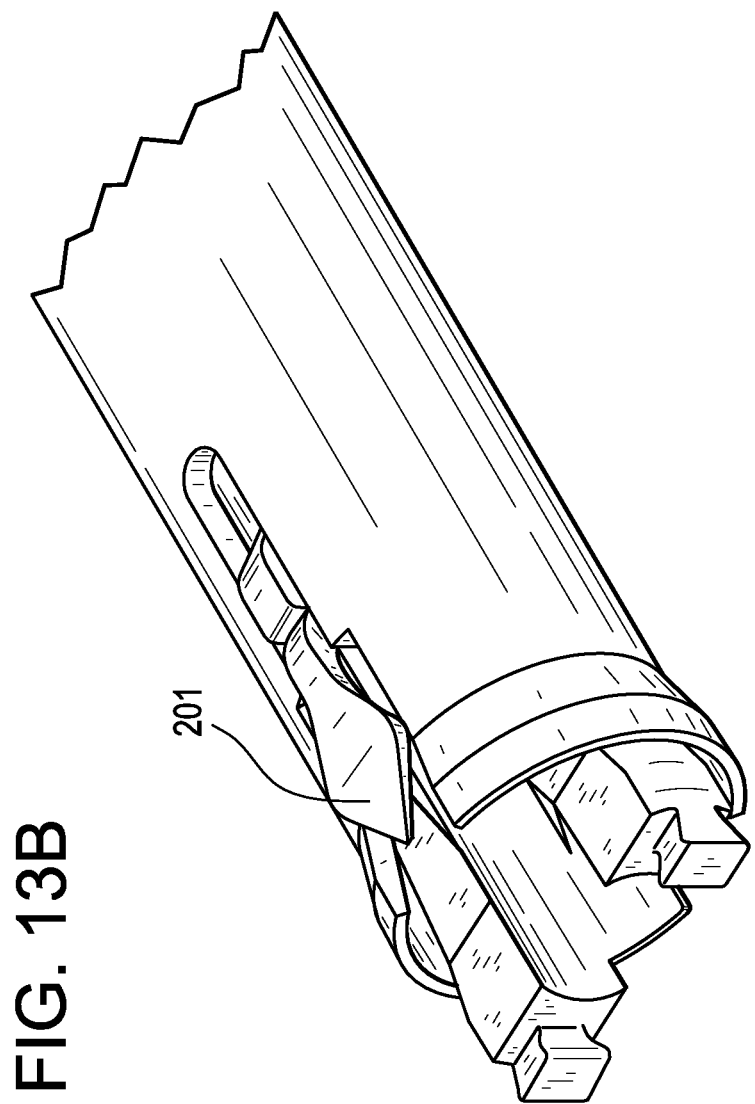
Figure 13C:
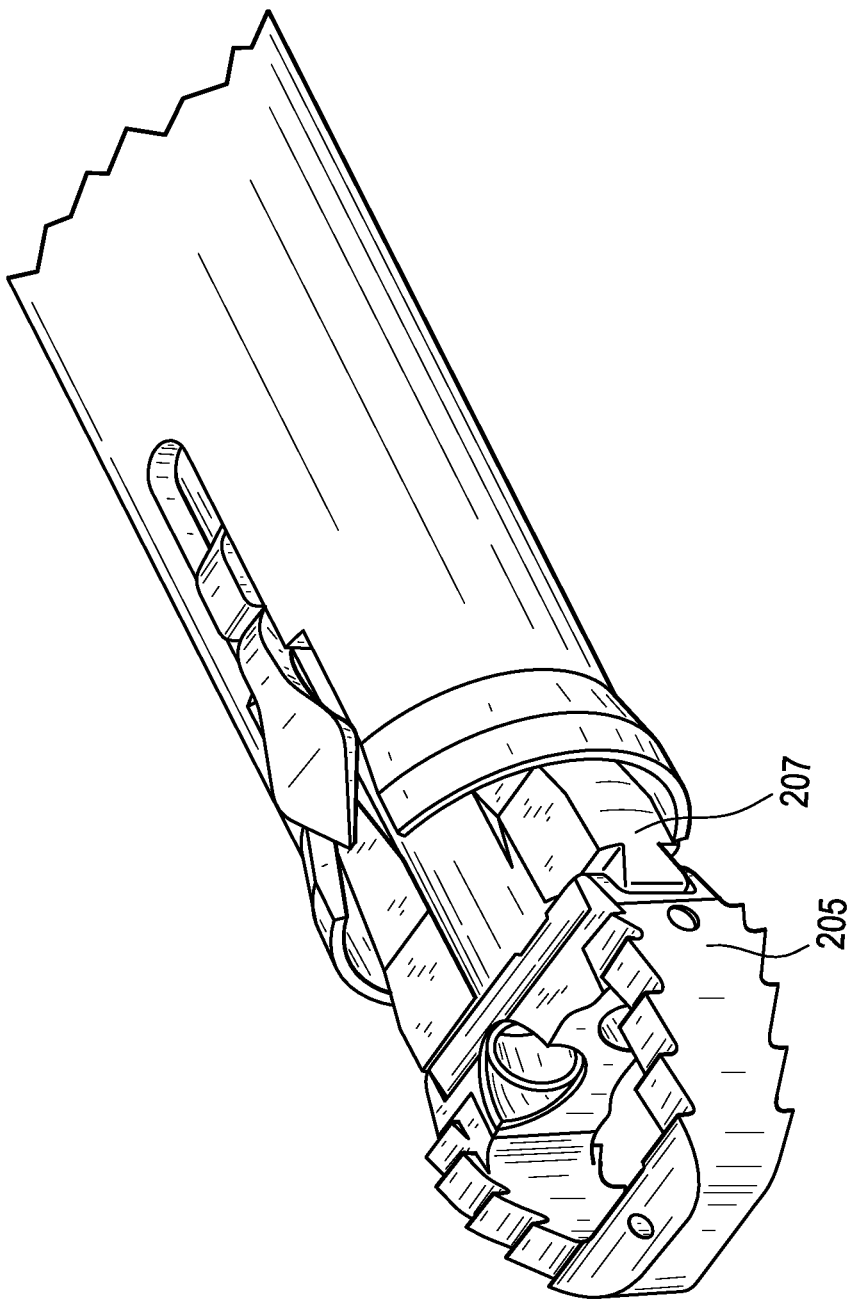
Figure 13D:
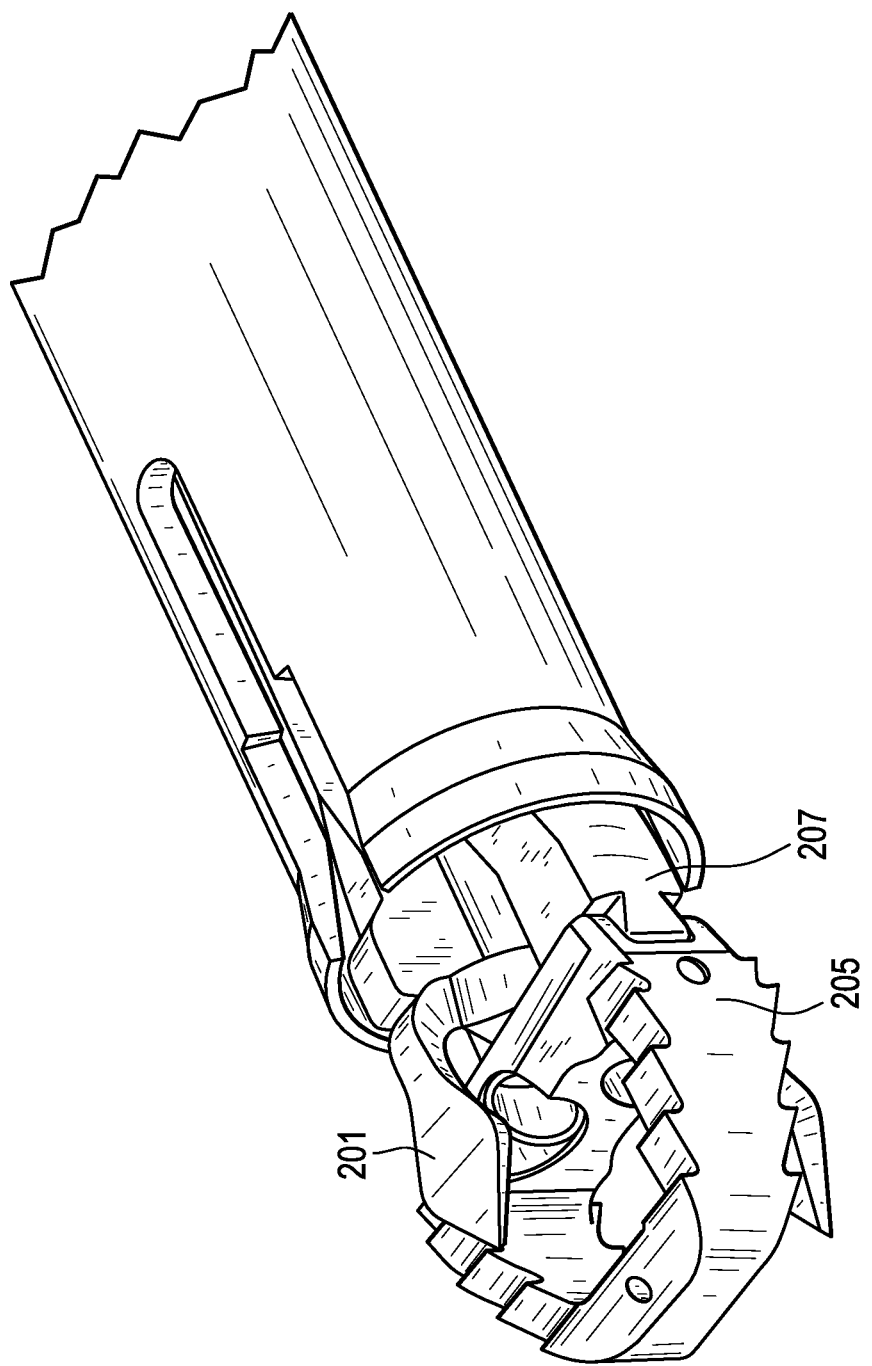

FIGS. 13a-d disclose one method of inserting the device of the present invention. In FIG. 13a, a staple 201 is shown mounted on the distal end of the inner grabber tip 203. In FIG. 13b, the staple 201 and inner grabber tip are retracted into the inserter cannula. Next, as shown in FIG. 13c, with the inner grabber tip and mounted staple retracted, a cage 205 of the present invention is mounted onto the outer grabber tip 207. The cage is then inserted into the intervertebral disc space while in this configuration. Lastly, now referring to FIG. 13d, the staple is deployed over the inserted cage as shown and thereby inserted into the opposed vertebral bodies. The staple can be made of conventional structural biomaterials. Typically, it is made of a metallic biomaterials such as titanium alloy, stainless steel, nitinol, or cobalt chrome.

In some embodiments, the anterior wall of the cage is made of a metallic material, such as titanium alloy, stainless steel, or cobalt chrome, while the remainder of the cage is made from a polymeric material or a structural allograft material. Alternatively, the device can be made entirely from any one of these specified materials.

If a metal is chosen as the material of construction, then the metal is preferably selected from the group consisting of nitinol, titanium, titanium alloys (such as Ti-6Al-4V), chrome alloys (such as CrCo or Cr—Co—Mo) and stainless steel.

If a polymer is chosen as a material of construction, then the polymer is preferably selected from the group consisting of polycarbonates, polyesters, (particularly aromatic esters such as polyalkylene terephthalates, polyamides; elastomers; polyalkenes; poly(vinyl fluoride); PTFE; polyarylethyl ketone PAEK; and mixtures thereof.

In embodiments in which a bone graft material is placed within the through hole of the device, the bone graft material can be selected from the group consisting of hydroxyapatite, tricalcium phosphate, allograft, and growth factors such as TGF-beta (and preferably BMPs—more preferably, rhGDF-5).

In some embodiments, a component is made of a stainless steel alloy, preferably BioDur® CCM Plus® Alloy available from Carpenter Specialty Alloys, Carpenter Technology Corporation of Wyomissing, Pa. In some embodiments, the component is made from a composite comprising carbon fiber. Composites comprising carbon fiber are advantageous in that they typically have a strength and stiffness that is superior to neat polymer materials such as a polyarylethyl ketone PAEK. In some embodiments, the component is made from a polymer composite such as a PEKK-carbon fiber composite.

Preferably, the composite comprising carbon fiber further comprises a polymer. Preferably, the polymer is a polyarylethyl ketone (PAEK). More preferably, the PAEK is selected from the group consisting of polyetherether ketone (PEEK), polyether ketone ketone (PEKK) and polyether ketone (PEK). In preferred embodiments, the PAEK is PEEK.

In some embodiments, the carbon fiber comprises between 1 vol % and 60 vol % (more preferably, between 10 vol % and 50 vol %) of the composite. In some embodiments, the polymer and carbon fibers are homogeneously mixed. In others, the material is a laminate. In some embodiments, the carbon fiber is present in a chopped state. Preferably, the chopped carbon fibers have a median length of between 1 mm and 12 mm, more preferably between 4.5 mm and 7.5 mm. In some embodiments, the carbon fiber is present as continuous strands.

In especially preferred embodiments, the composite comprises:
a) 40-99% (more preferably, 60-80 vol %) polyarylethyl ketone (PAEK), and
b) 1-60% (more preferably, 20-40 vol %) carbon fiber,
wherein the polyarylethyl ketone (PAEK) is selected from the group consisting of polyetherether ketone (PEEK), polyether ketone ketone (PEKK) and polyether ketone (PEK).

In some embodiments, the composite consists essentially of PAEK and carbon fiber. More preferably, the composite comprises 60-80 wt % PAEK and 20-40 wt % carbon fiber. Still more preferably the composite comprises 65-75 wt % PAEK and 25-35 wt % carbon fiber.

We claim:
1. An intervertebral fusion device consisting of:
  a) an intervertebral fusion cage comprising an anterior wall having an anterior face having a completely unthreaded recess therein, a posterior wall, a pair of side walls connecting the anterior and posterior walls, an upper surface, a lower surface, and a through hole extending from the upper surface to the lower surface, the cage having an anterior end,
b) a single staple comprising a first crossbar and first and second tynes extending therefrom, each tyne having a proximal portion and a distal portion, wherein the first crossbar of the staple is fully fixed in the recess in the anterior face of the anterior wall to create a zero profile, wherein the first tyne extends above the upper surface of the cage and the second tyne extends below the lower surface of the cage so that the first tyne is disposed substantially above the second tyne, wherein the distal portion of each tyne comprises a distal tip comprising a plurality of teeth extending from the tip, wherein the staple is detachable and contacts only an anterior half portion of the cage, and wherein the recess defines a window, and wherein the entire staple passes through the window of the recess in the anterior wall during insertion, wherein each tyne has a distal end having a concave face that faces the cage and a convex face that faces away from the cage, wherein, upon full deployment of the staple, the distal end of each tyne points posteriorly.

2. A two piece intervertebral fusion device consisting of:
a) an intervertebral fusion cage comprising an anterior wall having an anterior face having a completely unthreaded recess therein, a posterior wall, a pair of side walls connecting the anterior and posterior walls, an upper surface, a lower surface, and a through hole extending from the upper surface to the lower surface, the cage having an anterior end,
b) a single staple comprising a first crossbar and first and second tynes extending therefrom, wherein at least a portion of the first crossbar of the staple is fixed in the recess in the anterior face of the anterior wall, wherein the first tyne extends above the upper surface of the cage and the second tyne extends below the lower surface of the cage so that the first tyne is disposed substantially above the second tyne, wherein the staple is detachable and contacts only an anterior portion of the cage, and wherein the staple attachable to the cage by posterior motion relative to the cage wherein the first and second tynes pass through the cage, and wherein the recess defines a window, and wherein the entire staple passes through the window of the recess in the anterior wall during insertion, wherein each tyne has a distal end having a concave face that faces the cage and a convex face that faces away from the cage, wherein, upon full deployment of the staple, the distal end of each tyne points posteriorly.

* * * * *